(12) United States Patent  
Okabe et al.

(10) Patent No.: US 9,409,874 B2  
(45) Date of Patent: Aug. 9, 2016

(54) METHOD FOR PRODUCING 1,4-BENZOXAZINE COMPOUND

(71) Applicant: MITSUBISHI TANABE PHARMA CORPORATION, Osaka-shi, Osaka (JP)

(72) Inventors: Tomoyuki Okabe, Osaka (JP); Takeshi Hamada, Osaka (JP); Kaori Tomikawa, Osaka (JP); Yukie Okamoto, Osaka (JP); Toru Iijima, Osaka (JP); Hidenori Akatsuka, Osaka (JP); Kenichi Toyama, Osaka (JP); Atsushi Moroda, Osaka (JP); Yoshihiro Sugiura, Osaka (JP)

(73) Assignee: MITSUBISHI TANABE PHARMA CORPORATION, Osaka-Shi (JP)

( * ) Notice: Subject to any disclaimer, the term of this patent is extended or adjusted under 35 U.S.C. 154(b) by 0 days.

(21) Appl. No.: 14/420,276

(22) PCT Filed: Aug. 8, 2013

(86) PCT No.: PCT/JP2013/071446  
§ 371 (c)(1),  
(2) Date: Feb. 6, 2015

(87) PCT Pub. No.: WO2014/024950  
PCT Pub. Date: Feb. 13, 2014

(65) Prior Publication Data  
US 2015/0218113 A1     Aug. 6, 2015

(30) Foreign Application Priority Data

Aug. 8, 2012  (JP) .................................. 2012-176217  
Jan. 18, 2013  (JP) .................................. 2013-007041

(51) Int. Cl.  
*C07D 265/36*     (2006.01)

(52) U.S. Cl.  
CPC .................................. *C07D 265/36* (2013.01)

(58) Field of Classification Search  
CPC .................................................. C07D 265/36  
USPC ........................................................ 544/105  
See application file for complete search history.

(56) References Cited

FOREIGN PATENT DOCUMENTS

| JP | 2006-505575 A | 2/2006 |
| JP | 2008-115149 A | 5/2008 |
| JP | 2009-51830 A | 3/2009 |
| WO | WO 2004/037796 A2 | 5/2004 |
| WO | WO 2007/089034 A1 | 8/2007 |

OTHER PUBLICATIONS

Extended European Search Report for European Application No. 13828067.2 dated Dec. 11, 2015.

(Continued)

*Primary Examiner* — Kahsay Habte  
(74) *Attorney, Agent, or Firm* — Birch, Stewart, Kolasch & Birch, LLP

(57) ABSTRACT

The present invention provides an industrially advantageous method for producing a 1,4-benzoxazine compound useful as a medicine while avoiding safety and health risks. Specifically, the present invention provides a method for producing a 1,4-benzoxazine compound [A], which comprises the three steps in the following scheme, namely, a step of converting the amino group at 7-position in a compound [a] into a dimesylamino group, a step of coupling a compound [b] with a boronic acid compound, and a step of converting the 7-position in a compound [c] into a monomesylamino group.

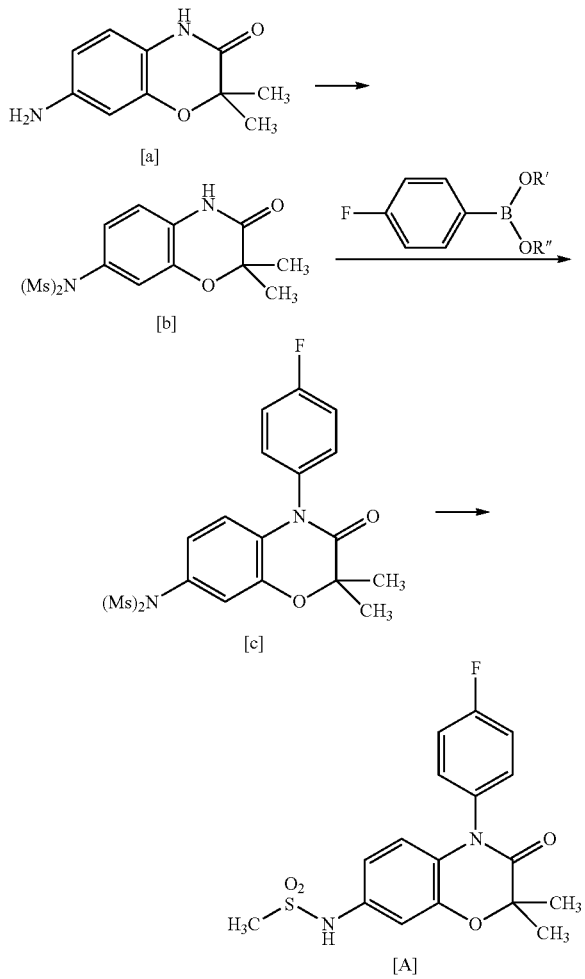

In the above scheme, Ms is a methanesulfonyl group, and each of R' and R" is a hydrogen atom etc.

6 Claims, 4 Drawing Sheets

(56) References Cited

OTHER PUBLICATIONS

Piotrowski, David W., "Mineralocorticoid Receptor Antagonists for the Treatment of Hypertension and Diabetic Nephropathy", J. of Medicinal Chemistry, vol. 55, No. 18, Aug. 6, 2012, pp. 7957-7966, XP55213613.

Byrn, Stephen et al., "Pharmaceutical Solids: A Strategic Approach to Regulatory Considerations," Pharmaceutical Research, vol. 12, No. 7, 1995, pp. 945-954.

English translation of International Preliminary Report on Patentability and Written Opinion mailed Feb. 19, 2015, in PCT International Application No. PCT/JP2013/071446.

English translation of International Search Report mailed Nov. 12, 2013, in International Application No. PCT/JP2013/071446.

METHOD FOR PRODUCING 1,4-BENZOXAZINE COMPOUND

TECHNICAL FIELD

The present invention relates to a novel method for producing a 1,4-benzoxazine compound which has an aldosterone receptor antagonistic action, and is useful as a medicine such as an antihypertensive or a diuretic.

BACKGROUND ART

The recent research on aldosterone has revealed that said hormone is produced not only by adrenal gland but also by other various organs such as heart, blood vessel or brain, and that its receptor is also widely distributed not only in cardiovascular tissue but also in other tissues. Further, aldosterone has been recognized not only as an exacerbation factor of hypertension, but also as a risk hormone which has various injurious actions on cardiovascular tissue. Under these circumstances, an aldosterone receptor antagonist has been found to have features such as a positive action on serious heart failure or acute myocardial infarction in a recent large clinical trial, and thus is expected to be a potential drug useful for establishing an effective therapy for cardiovascular diseases.

Patent Literature 1 discloses a compound of the following general formula [I]:

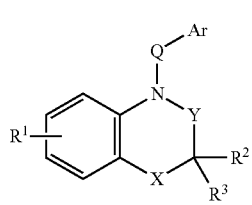

useful as an aldosterone antagonist. Among the compound [I] disclosed in said Patent Literature 1, for example, a compound of the following formula [A]:

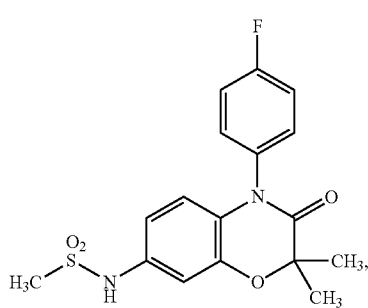

namely, N-[4-(4-fluorophenyl)-2,2-dimethyl-3-oxo-3,4-dihydro-2H-1,4-benzoxazin-7-yl]methanesulfonamide, is expected to be clinically used as an aldosterone receptor antagonist.

As a method for producing the above compound [A], Patent Literature 1 discloses the following synthetic method.

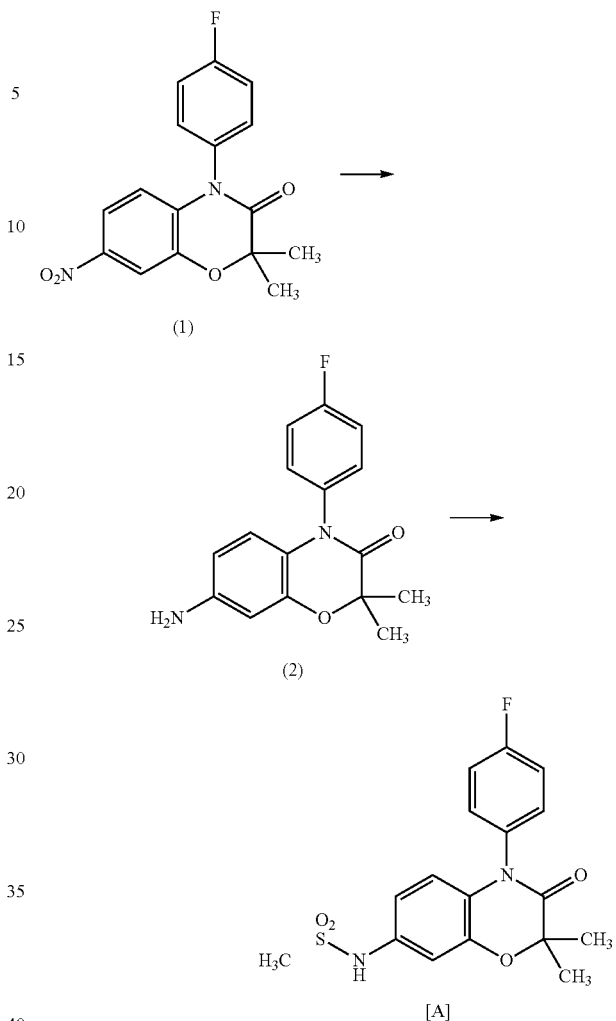

However, the final intermediate (2) in the above method has been confirmed to have a strong mutagenicity by the AMES test, and thus has a problem of carrying safety and health risks when used as a synthetic intermediate of a medicine. Therefore, as a synthetic method for producing the compound [A], it has been desired to establish an industrially advantageous method without carrying the above safety and health risks.

Also, in general, regarding a compound which is expected to be useful as a medicine, it is known that its physical properties (e.g., the presence or absence of an amorphous state, a crystal and a polymorph thereof, etc.) significantly affect the purity or stability (e.g., photostability and humidity stability, etc.) as an active pharmaceutical ingredient, the stability in a formulation, and the bioavailability when used as a medicine. Therefore, it is an important problem in the development of a medicine to obtain stably and on an industrial scale a single crystal of a medicinal compound having the above excellent physical properties. However, it is difficult to reasonably predict the presence or absence of a crystal and a polymorph thereof of a certain compound. Meanwhile, Patent Literature 1 discloses that the compound [A] was obtained as a powder material.

BACKGROUND ART DOCUMENTS

Patent Literatures

Patent Literature 1: WO2007/089034

SUMMARY OF THE INVENTION

Problems to be Solved by the Invention

The present invention provides a novel method for industrially advantageously producing the above compound [A] useful as a medicine. Furthermore, the present invention relates to novel crystal forms of the compound [A] which is preferable as a medicinal compound.

Means for Solving the Problems

The present inventors have carried out intensive studies for solving the above problems, and as a result, found that a synthetic method comprising the step in the following formula (i.e., a step of reacting a compound [b] with a boronic acid compound [d] to produce a compound [c]) can produce the target compound [A] in a high yield while avoiding safety and health risks (e.g., risks associated with the mutagenicity of the synthetic intermediates), and finally completed the present invention. Meanwhile, to the best of the applicant's knowledge, the following compound [b] and the compound [c] are novel compounds.

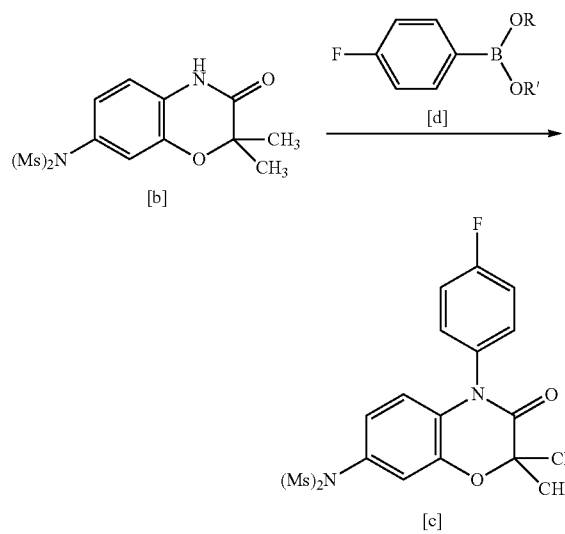

In the above scheme, Ms is a methanesulfonyl group, and R and R' are the same or different and each of them is a hydrogen atom or an alkyl group, or both of them combine together to form an alkylene group.

In addition to the above method, the present inventors have found that the compound [A] (a powder material) disclosed in Patent Literature 1 is present in a specific crystal form (Form D crystal), and further found that the compound [A] has multiple crystal forms (crystal polymorphs) different from the Form D crystal, said novel crystals have higher stability as compared to the Form D crystal, and also have desired profiles as a medicinal compound (i.e., an active pharmaceutical ingredient), and finally completed the present invention.

Namely, the present invention relates to:

[1] a method for producing a 1,4-benzoxazine compound of the following formula [A]:

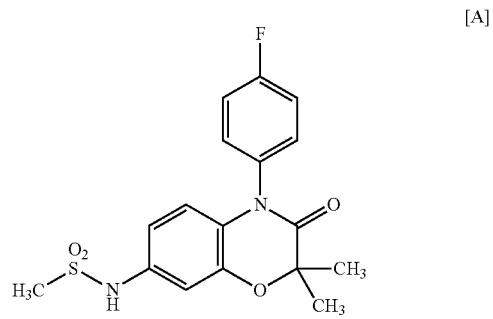

which comprises the following steps of:

(step a) reacting a compound of the following formula [a]:

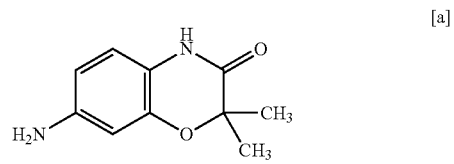

with methanesulfonyl halide in the presence of a base to produce a compound of the following formula [b]:

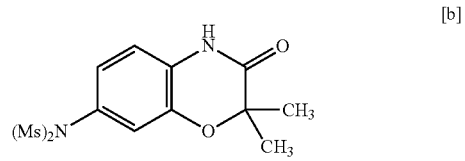

wherein Ms is a methanesulfonyl group, (step b) reacting said compound [b] with a boronic acid compound of the following formula [d]:

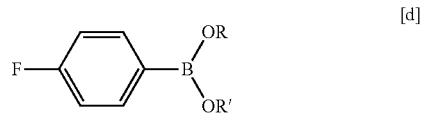

wherein R and R' are the same or different and each of them is a hydrogen atom or an alkyl group, or both of them combine together to form an alkylene group, or an equivalent thereof, in the presence of a copper catalyst, in the presence or absence of a base, and in the presence or absence of a ligand to produce a compound of the following formula [c]:

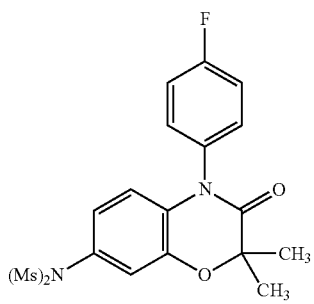

wherein the symbol is the same as defined above,
and (step c) converting the substituent at 7-position (dimesylamino group) in said compound [c] into a monomesylamino group to produce the compound of the above formula [A];

[2] the method according to the above item [1], wherein the methanesulfonyl halide is methanesulfonyl chloride;

[3] the method according to the above item [1], wherein the compound [d] is a compound of the following formula:

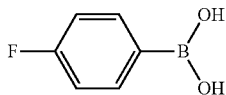

or an equivalent thereof;

[4] the method according to the above item [1], [2] or [3], characterized in that (1) the step a is carried out in a solvent selected from the group consisting of acetonitrile, methyl ethyl ketone, ethyl acetate, tetrahydrofuran and acetone, and in the presence of a base selected from triethylamine, tetramethylethylenediamine and 1,8-diazabicyclo[5.4.0]undec-7-ene, (2) the step b is carried out in a solvent selected from dimethylsulfoxide and N,N-dimethylacetamide, in the presence of a copper catalyst selected from the group consisting of copper acetate, copper halide, copper nitrate and a copper salt of trifluoromethanesulfonic acid, in the presence or absence of one or more bases selected from triethylamine, diisopropylethylamine, tributylamine, tripropylamine, trioctylamine, dimethylbenzylamine, 1,8-diazabicyclo[5.4.0]undec-7-ene, N-ethylmorpholine, N-methylmorpholine, sodium hydrogen carbonate and an aqueous ammonia, in the presence or absence of one or more ligands selected from dimethylaminopyridine, 2-aminopyridine, 4-methylpyridine, 2,6-dimethylpyridine, 3,5-dimethylpyridine, pyridine, N-methylimidazole, N-butylimidazole and pyrazine, and under oxygen supply to the reaction system, and (3) the step c is carried out in a solvent selected from ethanol, isopropanol, n-propanol, acetone, methyl ethyl ketone and dimethylsulfoxide or a mixture of said solvent and water, and in the presence of a base selected from potassium carbonate and sodium hydroxide;

[5] a method for producing a compound of the following formula [A]:

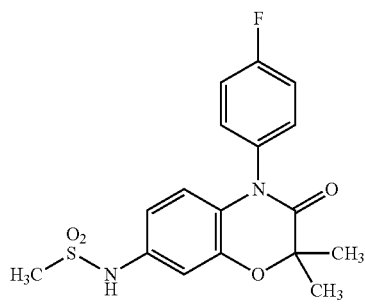

which comprises the step of converting the substituent at 7-position (dimesylamino group) in a compound of the following formula [c]:

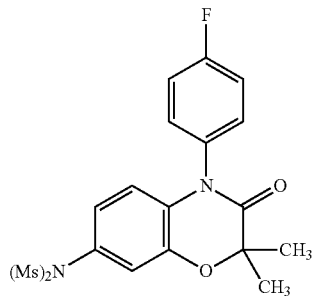

wherein Ms is a methanesulfonyl group,
into a monomesylamino group;

[6] the method according to the above item [5], characterized in that the conversion of the substituent at 7-position (dimesylamino group) into the monomesylamino group is carried out in a solvent selected from ethanol, isopropanol, n-propanol, acetone, methyl ethyl ketone and dimethylsulfoxide or a mixture of said solvent and water, and in the presence of a base selected from potassium carbonate and sodium hydroxide;

[7] a method for producing a compound of the following formula [c]:

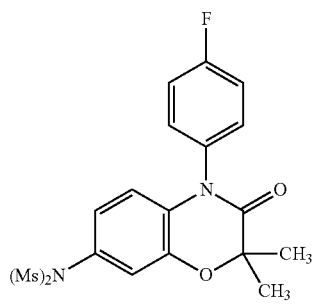

wherein Ms is a methanesulfonyl group,
which comprises the following steps of:
(step a) reacting a compound of the following formula [a]:

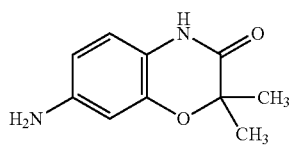

with methanesulfonyl halide in the presence of a base to produce a compound of the following formula [b]:

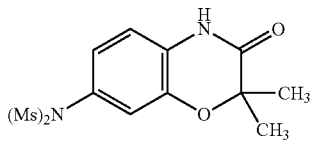

wherein the symbol is the same as defined above, and (step b) reacting said compound [b] with a boronic acid compound of the following formula [d]:

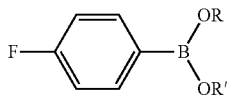

wherein R and R' are the same or different and each of them is a hydrogen atom or an alkyl group, or both of them combine together to form an alkylene group, or an equivalent thereof, in the presence of a copper catalyst, in the presence or absence of a base, and in the presence or absence of a ligand;

[8] the method according to the above item [7], characterized in that (1) the step a is carried out in a solvent selected from the group consisting of acetonitrile, methyl ethyl ketone, ethyl acetate, tetrahydrofuran and acetone, and in the presence of a base selected from triethylamine, tetramethylethylenediamine and 1,8-diazabicyclo[5.4.0]undec-7-ene, and (2) the step b is carried out in a solvent selected from dimethylsulfoxide and N,N-dimethylacetamide, in the presence of a copper catalyst selected from the group consisting of copper acetate, copper halide, copper nitrate and a copper salt of trifluoromethanesulfonic acid, in the presence or absence of one or more bases selected from triethylamine, diisopropylethylamine, tributylamine, tripropylamine, trioctylamine, dimethylbenzylamine, 1,8-diazabicyclo[5.4.0]undec-7-ene, N-ethylmorpholine, N-methylmorpholine, sodium hydrogen carbonate and an aqueous ammonia, in the presence or absence of one or more ligands selected from dimethylaminopyridine, 2-aminopyridine, 4-methylpyridine, 2,6-dimethylpyridine, 3,5-dimethylpyridine, pyridine, N-methylimidazole, N-butylimidazole and pyrazine, and under oxygen supply to the reaction system;

[9] a method for producing a compound of the following formula [c]:

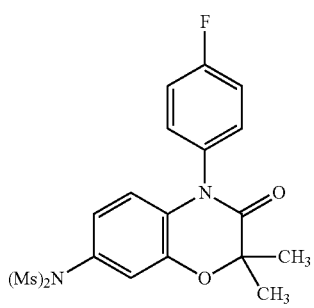

wherein Ms is a methanesulfonyl group, which comprises the step of reacting a compound of the following formula [b]:

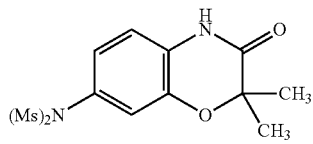

wherein the symbol is the same as defined above, with a boronic acid compound of the following formula [d]:

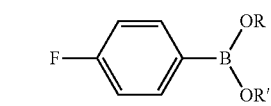

wherein R and R' are the same or different and each of them is a hydrogen atom or an alkyl group, or both of them combine together to form an alkylene group, or an equivalent thereof, in the presence of a copper catalyst, in the presence or absence of a base, and in the presence or absence of a ligand;

[10] the method according to the above item [9], characterized in that the coupling reaction of the compound [b] with the compound [d] is carried out in a solvent selected from dimethylsulfoxide and N,N-dimethylacetamide, in the presence of a copper catalyst selected from the group consisting of copper acetate, copper halide, copper nitrate and a copper salt of trifluoromethanesulfonic acid, in the presence or absence of one or more bases selected from triethylamine, diisopropylethylamine, tributylamine, tripropylamine, trioctylamine, dimethylbenzylamine, 1,8-diazabicyclo[5.4.0]undec-7-ene, N-ethylmorpholine, N-methylmorpholine, sodium hydrogen carbonate and an aqueous ammonia, in the presence or absence of one or more ligands selected from dimethylaminopyridine, 2-aminopyridine, 4-methylpyridine, 2,6-dimethylpyridine, 3,5-dimethylpyridine, pyridine, N-methylimidazole, N-butylimidazole and pyrazine, and under oxygen supply to the reaction system;

[11] a compound of the following formula [b]:

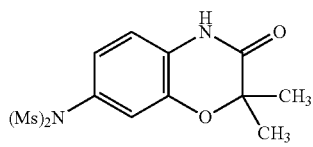

wherein Ms is a methanesulfonyl group;
and

[12] a compound of the following formula [c]:

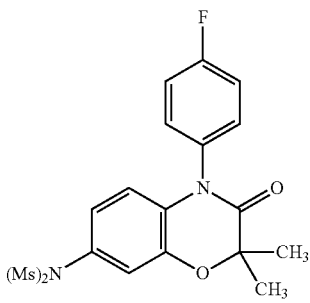

[c]

wherein Ms is a methanesulfonyl group.

Further, the present invention relates to:

[13] a crystal (Form A crystal) of N-[4-(4-fluorophenyl)-2,2-dimethyl-3-oxo-3,4-dihydro-2H-1,4-benzoxazin-7-yl]methanesulfonamide, which has at least one diffraction peak at 6.7° to 11.0°, and has diffraction peaks at 18.1° and 23.7° as the diffraction angle (2θ±0.2°) in the X-ray powder diffraction;

[14] the crystal of N-[4-(4-fluorophenyl)-2,2-dimethyl-3-oxo-3,4-dihydro-2H-1,4-benzoxazin-7-yl]methanesulfonamide according to the above item [13], which has an additional diffraction peak at 10.2° as the diffraction angle (2θ±0.2°);

[15] a crystal (Form B crystal) of N-[4-(4-fluorophenyl)-2,2-dimethyl-3-oxo-3,4-dihydro-2H-1,4-benzoxazin-7-yl]methanesulfonamide, which has at least one diffraction peak at 6.7° to 11.0°, and has diffraction peaks at 14.8° and 18.3° as the diffraction angle (2θ±0.2°) in the X-ray powder diffraction;

[16] the crystal of N-[4-(4-fluorophenyl)-2,2-dimethyl-3-oxo-3,4-dihydro-2H-1,4-benzoxazin-7-yl]methanesulfonamide according to the above item [15], which has additional diffraction peaks at 10.8° and 23.2° as the diffraction angle (2θ±0.2°);

[17] a crystal (Form C crystal) of a dimethylsulfoxide monosolvate of N-[4-(4-fluorophenyl)-2,2-dimethyl-3-oxo-3,4-dihydro-2H-1,4-benzoxazin-7-yl]methanesulfonamide, which has diffraction peaks at 19.3° and 29.6° as the diffraction angle (2θ±0.2°) in the X-ray powder diffraction;

[18] the crystal of the dimethylsulfoxide monosolvate of N-[4-(4-fluorophenyl)-2,2-dimethyl-3-oxo-3,4-dihydro-2H-1,4-benzoxazin-7-yl]methanesulfonamide according to the above item [17], which has an additional diffraction peak at 11.3° as the diffraction angle (2θ±0.2°);

[19] a pharmaceutical composition comprising the crystal of N-[4-(4-fluorophenyl)-2,2-dimethyl-3-oxo-3,4-dihydro-2H-1,4-benzoxazin-7-yl]methanesulfonamide or a dimethylsulfoxide monosolvate thereof according to any one of the above items [13] to [18] and a pharmacologically acceptable carrier;

[20] the pharmaceutical composition according to the above item [19], which is a preventive or therapeutic agent for various diseases or disease states caused by enhanced MR activity and/or elevated aldosterone level;

[21] the pharmaceutical composition according to the above item [19], which is a preventive or therapeutic agent for hypertension, heart failure, myocardial infarction, angina, cardiac hypertrophy, myocarditis, myocardial/vascular fibrosis, baroreceptor dysfunction, volume overload or arrhythmia;

[22] the pharmaceutical composition according to the above item [19], which is a preventive or therapeutic agent for primary/secondary aldosteronism, Addison's disease, Cushing's syndrome or Bartter's syndrome;

[23] the pharmaceutical composition according to the above item [19], which is a preventive or therapeutic agent for a renal disease;

[24] the pharmaceutical composition according to the above item [23], wherein the renal disease is diabetic nephropathy;

[25] a method for producing a Form A crystal of N-[4-(4-fluorophenyl)-2,2-dimethyl-3-oxo-3,4-dihydro-2H-1,4-benzoxazin-7-yl]methanesulfonamide having at least one diffraction peak at 6.7° to 11.0°, and having diffraction peaks at 18.1° and 23.7° as the diffraction angle (2θ±0.2°) in the X-ray powder diffraction, which comprises the step of heating a crystal (Form D crystal) of N-[4-(4-fluorophenyl)-2,2-dimethyl-3-oxo-3,4-dihydro-2H-1,4-benzoxazin-7-yl]methanesulfonamide having no diffraction peak at 6.7° to 11.0°, but having diffraction peaks at 6.0°, 11.9°, 17.0°, 17.6° and 19.0° as the diffraction angle (2θ±0.2°), or a crystal (Form B crystal) of N-[4-(4-fluorophenyl)-2,2-dimethyl-3-oxo-3,4-dihydro-2H-1,4-benzoxazin-7-yl]methanesulfonamide having at least one diffraction peak at 6.7° to 11.0°, and having diffraction peaks at 14.8° and 18.3° as the diffraction angle (2θ±0.2°) in the X-ray powder diffraction in a liquid medium or in the absence of a medium; and

[26] the method for producing the Form A crystal of N-[4-(4-fluorophenyl)-2,2-dimethyl-3-oxo-3,4-dihydro-2H-1,4-henzoxazin-7-yl]methanesulfonamide according to the above item [25], characterized by heating the Form B crystal in ethanol as the liquid medium at 75° C. to 85° C.

Effects of the Invention

By using the method of the present invention, the 1,4-benzoxazine compound [A] useful as a medicine can be prepared in a high yield. Also, the method of the present invention can use an intermediate having lower safety and health risks (e.g., mutagenicity etc.), and thus can be an industrially advantageous method.

The novel crystals of the present invention (Form A crystal, Form B crystal and Form C crystal) are highly stable. Especially, the Form A crystal does not transform to an amorphous state or other crystal form by a factor such as heating and is non-hygroscopic, and thus has preferable features as a crystal form of a medicinal compound. Further, the Form A crystal is also characterized in that it is highly stable in a formulation, and thus is a preferable crystal form as an active pharmaceutical ingredient.

Figure 1:
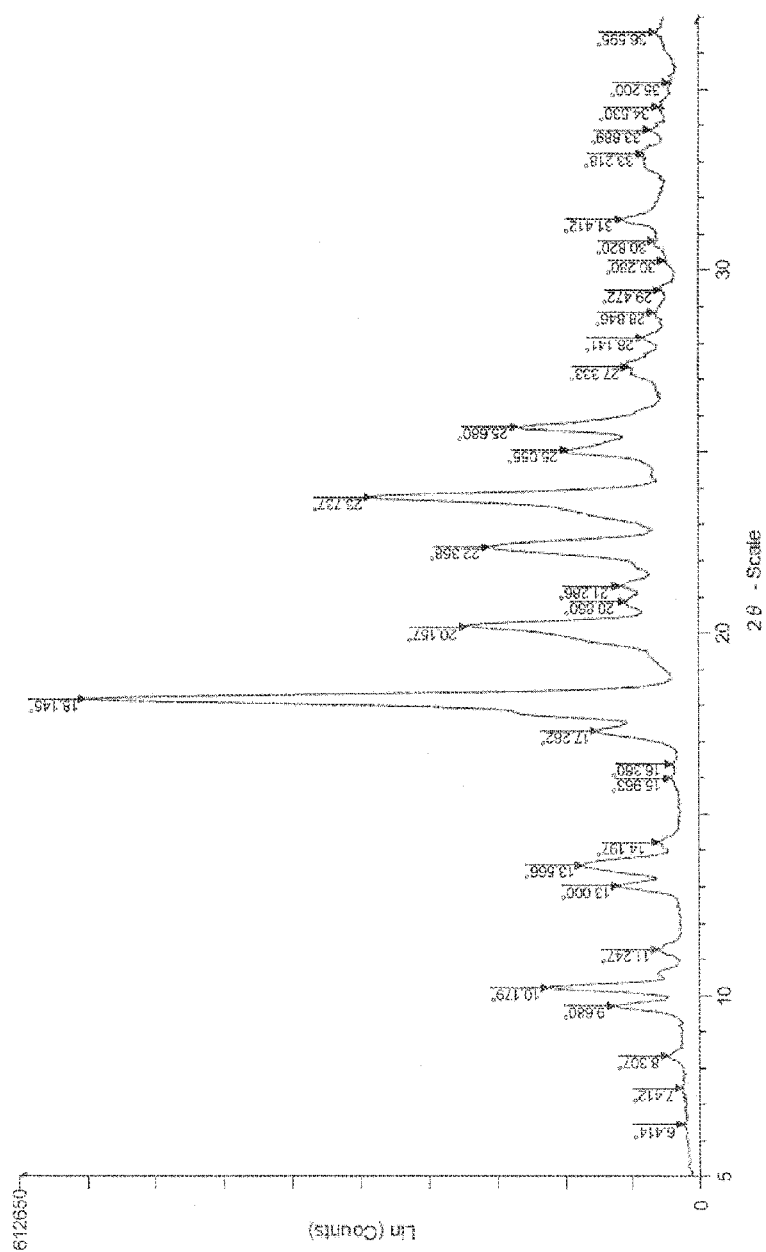
FIG. 1 shows the X-ray powder diffraction pattern of the Form A crystal of the compound [A].

EMBODIMENTS TO CARRY OUT THE INVENTION (Step a)

The reaction of the compound [a] with methanesulfonyl halide can be carried out in a solvent, and in the presence of a base. As the methanesulfonyl halide, methanesulfonyl chloride is preferable. The solvent may be any solvent as long as it does not disturb the present reaction, and examples of the solvent include an aromatic hydrocarbon such as toluene, an amide such as N,N-dimethylacetamide, a nitrile such as acetonitrile, a ketone such as acetone or methyl ethyl ketone, an ester such as ethyl acetate, an ether such as tetrahydrofuran, and the like. Among them, acetonitrile, methyl ethyl ketone, ethyl acetate, tetrahydrofuran and acetone are preferable, and acetonitrile is more preferable. Examples of the base include a tertiary amine such as triethylamine, diisopropylethylamine or 1,8-diazabicyclo[5.4.0]undec-7-ene (DBU), an alkylenediamine such as tetramethylethylenediamine (TMEDA), Proton Sponge (registered trademark), and the like, and among them, triethylamine, tetramethylethylenediamine and 1,8-diazabicyclo[5.4.0]undec-7-ene are preferable, and triethylamine is more preferable. Amount of the methanesulfonyl halide to be used is 1.0 to 5.0 molar equivalent, preferably 2.0 to 3.0 molar equivalent to the compound [a]. Amount of the base to be used is 1.0 to 5.0 molar equivalent, preferably 2.0 to 3.0 molar equivalent to the compound [a]. The methanesulfonyl halide and the base may be added to the reaction system in two or three portions depending on the reaction progress. Amount of the solvent to be used is 10 to 20 V/W, preferably 10 to 15 V/W to the compound [a]. The present reaction can be carried out at 0 to 50° C., preferably 30 to 50° C. The reaction product, i.e., the compound [b], can be obtained in a high purity by adding water to the reaction mixture, followed by carrying out a solid-liquid separation.

(Step b)

The reaction (coupling) of the compound [b] with the boronic acid compound [d] can be carried out in a solvent, in the presence of a copper catalyst, in the presence or absence of a base, and in the presence or absence of a ligand. The solvent may be any solvent as long as it does not disturb the present reaction, and examples of the solvent include an ether such as tetrahydrofuran, a ketone such as acetone or methyl ethyl ketone, an amide such as N,N-dimethylacetamide, a nitrile such as acetonitrile, dimethylsulfoxide, and the like. Among them, dimethylsulfoxide and N,N-dimethylacetamide are preferable, and dimethylsulfoxide is more preferable. Examples of the copper catalyst include a copper compound such as a copper acetate (copper(I) acetate or copper (II) acetate), a copper halide (copper chloride, copper bromide, copper iodide, etc.), copper sulfate, copper nitrate, copper(II) oxide, copper, copper-carbon or a copper salt of trifluoromethanesulfonic acid ($Cu(OTf)_2$ trihydrate), and among them, copper acetate, copper halide, copper nitrate and a copper salt of trifluoromethanesulfonic acid are preferable, and copper(II) acetate is more preferable. Said copper (II) acetate may be used in the form of a hydrate. Examples of the base include a tertiary amine such as triethylamine, diisopropylethylamine, tributylamine, tripropylamine, trioctylamine, dimethylbenzylamine, 1,8-diazabicyclo[5.4.0]undec-7-ene, N-ethylmorpholine or N-methylmorpholine, a pyridine such as pyridine or dimethylaminopyridine, an alkali metal base such as sodium hydrogen carbonate or sodium acetate, tetramethylethylenediamine, 1,4-diazabicyclo[2.2.2]octane (DABCO), ammonium acetate, an aqueous ammonia, a mixture thereof, and the like, and among them, triethylamine, diisopropylethylamine, tributylamine, tripropylamine, trioctylamine, dimethylbenzylamine, 1,8-diazabicyclo[5.4.0]undec-7-ene, N-ethylmorpholine, N-methylmorpholine, sodium hydrogen carbonate, an aqueous ammonia and a mixture thereof are preferable, and triethylamine, tributylamine, and a mixture thereof are more preferable. Examples of the ligand include a pyridine such as dimethylaminopyridine (DMAP), 2-aminopyridine, 4-methylpyridine (4-picoline), 2,6-dimethylpyridine (2,6-lutidine), 3,5-dimethylpyridine (3,5-lutidine), 2,4,6-trimethylpyridine (2,4,6-collidine) or pyridine, an imidazole such as 1,2-dimethylimidazole, N-methylimidazole (NMI) or N-butylimidazole, 1,4-diazabicyclo[2.2.2]octane (DABCO), pyrazine, a mixture thereof, and the like, and among them, dimethylaminopyridine, 2-aminopyridine, 4-methylpyridine, 2,6-dimethylpyridine, 3,5-dimethylpyridine, pyridine, N-methylimidazole, N-butylimidazole and pyrazine are preferable, dimethylaminopyridine, N-methylimidazole, 4-methylpyridine, N-butylimidazole and pyridine are more preferable, and N-methylimidazole and 4-methylpyridine are particularly preferable. Amount of the boronic acid compound [d] to be used is 1.0 to 3.0 molar equivalent, preferably 1.0 to 2.0 molar equivalent to the compound [b]. Examples of the equivalent of the boronic acid compound [d] and [d–1] include a boroxine compound of the following formula:

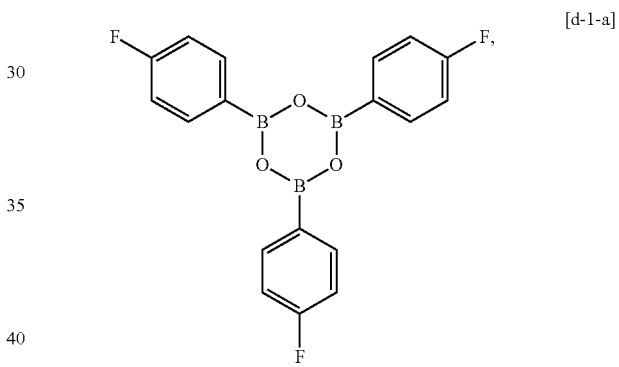

[d-1-a]

and the amount to be used is 0.7 to 1.7 molar equivalent, preferably 0.7 to 1.5 molar equivalent to the compound [b]. Amount of the copper catalyst to be used is 0.01 to 1.5 molar equivalent, preferably 0.1 to 1.0 molar equivalent in terms of copper amount to the compound [b]. When the base is used, the amount to be used is 0.4 to 3.0 molar equivalent, preferably 0.8 to 2.0 molar equivalent to the compound [b]. When the ligand is used, the amount to be used is 0.01 to 1.0 molar equivalent, preferably 0.1 to 0.5 molar equivalent to the compound [b]. Amount of the solvent to be used is 5 to 20 V/W, preferably 5 to 15 V/W to the compound [b]. The present reaction can be carried out at 15 to 60° C., preferably 15 to 30° C.

The present reaction is preferably carried out under oxygen supply (e.g., air induction etc.) to the reaction system.

The separation of the compound [c] from the above reaction mixture can be carried out by a conventional solid-liquid separation method. For example, the compound [c] can be obtained as a crystal by (1) adding methanol and an acid (e.g., aqueous hydrochloric acid solution etc.) to the reaction mixture, followed by collecting the precipitated crystals, then washing them with water and methanol etc. and drying them, or (2) adding dropwise the reaction mixture to a mixed solution of dimethylsulfoxide/water/an acid (e.g., aqueous hydrochloric acid solution etc.), followed by collecting the precipitated crystals, then washing them successively with a mixed solution of dimethylsulfoxide/water and water, and drying them.

The compound [c] is also characterized in that it is easily crystallized, and stable to the environmental factors (e.g., acid and temperature) in crystallization. Also, the compound [c] has lower mutagenicity, and thus is preferable as a synthetic intermediate of a medicinal compound.

(Step c)

The conversion of the substituent at 7-position (dimesylamino group) in the compound [c] into the monomesylamino group can be carried out by treating said compound [c] with a base in a solvent. The solvent may be any solvent as long as it does not disturb the present reaction, and examples of the solvent include an alcohol such as ethanol, n-propanol or isopropanol, a ketone such as acetone or methyl ethyl ketone, an ether such as tetrahydrofuran, dimethylsulfoxide, a mixed solvent of one or more of these organic solvents and water, and the like. Among them, ethanol, n-propanol, isopropanol, acetone, methyl ethyl ketone, dimethylsulfoxide, and a mixed solvent of one or more of these organic solvents and water are preferable. Examples of the base include an alkali metal carbonate such as potassium carbonate or sodium carbonate, an alkali metal hydroxide such as sodium hydroxide, potassium hydroxide or lithium hydroxide, potassium phosphate, tetrabutylammonium fluoride, and the like, and among them, potassium carbonate and sodium hydroxide are preferable. Amount of the base to be used is 1.0 to 5.0 molar equivalent, preferably 1.5 to 3.0 molar equivalent to the compound [c]. Amount of the solvent to be used is 5 to 20 V/W, preferably 5 to 10 V/W to the compound [c]. The present reaction can be carried out at 15 to 50° C., preferably 20 to 30° C.

The compound [A] can be separated from the above reaction mixture by a conventional solid-liquid separation method. For example, the compound [A] can be obtained as crystals by adding an acid (e.g., aqueous hydrochloric acid solution etc.) to the reaction mixture for neutralization, followed by collecting the precipitated crystals, then washing them with water and drying them. If necessary, the reaction mixture may be treated with activated carbon for the purpose of removal of by-products, decolorization, or the like.

The compound [A] in a desired crystal form can be obtained by appropriately selecting the solvent used in the above (step c) reaction. For example, when a ketone such as acetone or methyl ethyl ketone, dimethylsulfoxide or a mixed solvent of one or more of these organic solvents and water is used as the reaction solvent, the target compound [A] can be obtained mainly as the Form A crystal. When a mixed solvent of an organic solvent and water is used, the mixture ratio of water (V/V) is about 5% to about 50%, preferably about 30% to about 40%.

When an alcohol such as ethanol, n-propanol or isopropanol, dimethylsulfoxide, or a mixed solvent of one or more of these organic solvents and water is used as the reaction solvent, the target compound [A] can be obtained mainly as the Form B crystal or the Form D crystal.

Furthermore, the present inventors have confirmed by an experiment for screening crystal forms that the compound [A] can be present as the Form C crystal (a dimethylsulfoxide monosolvate). The Form C crystal of the compound [A] can be obtained by preparing a solution of said compound in dimethylsulfoxide, allowing said solution to stand for a certain period of time, then collecting the precipitated crystals by filtration, and drying them.

When the compound [A] obtained by the above method of the present invention is present as the Form B or Form D crystal, the Form A crystal of the compound [A] can be obtained, for example, by heating under reflux (75° C. to 85° C.) a suspension of said Form B or Form D crystal in ethanol for 2 to 15 hours, then cooling it, and collecting the crystals. Meanwhile, when the compound [A] obtained by the method of the present invention is present as the Form C crystal, the Form B crystal can be obtained by suspending said Form C crystal in water, stirring it, and then collecting the crystals.

Furthermore, the Form A crystal can also be obtained by heating the Form B crystal or the Form D crystal at 160° C. to 230° C.

As mentioned above, it has been confirmed that the compound [A] has four crystal polymorphs. Among these four crystal polymorphs, the Form A crystal, the Form B crystal and the Form C crystal are novel crystal forms.

Form A Crystal of Compound [A]:

The Form A crystal of the present invention is a crystal of N-[4-(4-fluorophenyl)-2,2-dimethyl-3-oxo-3,4-dihydro-2H-1,4-benzoxazin-7-yl]methanesulfonamide which has at least one diffraction peak at 6.7° to 11.0°, and has diffraction peaks at 18.1° and 23.7° as the diffraction angle (2θ±0.2°) in the X-ray powder diffraction (CuKα radiation). More specifically, said crystal is an anhydrous crystal having no adhesion water, and has diffraction peaks at 10.2°, 18.1°, 20.2° and 23.7° as the diffraction angle (2θ±0.2°) in the above X-ray powder diffraction. Still more specifically, said crystal has diffraction peaks at 8.3°, 9.7°, 10.2°, 13.0°, 13.6°, 18.1°, 20.2°, 22.4°, 23.7°, 25.1° and 25.7° as the diffraction angle (2θ±0.2°) in the above X-ray powder diffraction. Particularly specifically, said Form A crystal has diffraction peaks in the diffraction angles (2θ) shown in Table 1 described below in the above X-ray powder diffraction.

Also, the Form A crystal of the present invention has an endothermic peak at about 238° C. in the differential scanning calorimetry (DSC).

Form B Crystal of Compound [A]:

The Form B crystal of the present invention is a crystal of N-[4-(4-fluorophenyl)-2,2-dimethyl-3-oxo-3,4-dihydro-2H-1,4-benzoxazin-7-yl]methanesulfonamide which has at least one diffraction peak at 6.7° to 11.0°, and has diffraction peaks at 14.8° and 18.3° as the diffraction angle (2θ±0.2°) in the X-ray powder diffraction (CuKα radiation). More specifically, said crystal is an anhydrous crystal having no adhesion water, and has diffraction peaks at 10.8°, 14.8°, 18.3° and 23.2° as the diffraction angle (2θ±0.2°) in the above X-ray powder diffraction. Still more specifically, said crystal has diffraction peaks at 7.5°, 10.2°, 10.8°, 14.8°, 15.9°, 16.9°, 18.3°, 19.3°, 21.5°, 23.2°, 25.6° and 29.1° as the diffraction angle (2θ±0.2°) in the above X-ray powder diffraction. Particularly specifically, the Form B crystal of the present invention has diffraction peaks in the diffraction angles (2θ) shown in Table 2 described below in the above X-ray powder diffraction.

Form C Crystal of Compound [A]:

The Form C crystal of the present invention is a crystal of a dimethylsulfoxide monosolvate of N-[4-(4-fluorophenyl)-2,2-dimethyl-3-oxo-3,4-dihydro-2H-1,4-benzoxazin-7-yl]methanesulfonamide which has diffraction peaks at 19.3° and 29.6° as the diffraction angle (2θ±0.2°) in the X-ray powder diffraction (CuKα radiation). More specifically, said crystal has diffraction peaks at 11.3°, 19.3° and 29.6° as the diffraction angle (2θ±0.2°) in the above X-ray powder diffraction. Still more specifically, said crystal has diffraction peaks at 11.3°, 13.0°, 15.7°, 17.0°, 17.8°, 19.3°, 21.2°, 22.4°, 25.1°, 27.5° and 29.6° as the diffraction angle (2θ±0.2°) in the above X-ray powder diffraction. Particularly specifically, the Form C crystal of the present invention has diffraction peaks in the diffraction angles (2θ) shown in Table 3 described below in the above X-ray powder diffraction.

The crystals of the present invention obtained by the above method have preferable features as crystal forms of a medicinal compound. For example, the Form A crystal is characterized in that it has low hygroscopicity, and hardly makes a transition to other crystal form by heating, and thus is particularly preferable as a crystal form of the compound [A]. Furthermore, the Form A crystal is also characterized by its high stability in a formulation.

The Form B crystal is characterized in that it has low hygroscopicity, and higher thermostability as compared to the crystal (Form D crystal) of the compound [A] disclosed in Patent Literature 1, and thus is one of the preferable crystal forms of the compound [A]. Also, said Form B crystal can be converted into the Form A crystal by heating (75° C. to 85° C.) in a liquid medium (e.g., an organic solvent such as ethanol), and thus is also useful as a precursor of the target substance (Form A crystal) of the above method of the present invention.

While the Form C crystal is obtained as a dimethylsulfoxide monosolvate, said crystal can be easily converted into the Form B crystal by washing with water and drying, and thus is useful as a precursor of the Form B crystal.

Meanwhile, as is clear from the X-ray powder diffraction pattern (CuKα radiation) (FIG. 4), the crystal (Form D crystal) of the compound [A] (N-[4-(4-fluorophenyl)-2,2-dimethyl-3-oxo-3,4-dihydro-2H-1,4-benzoxazin-7-yl]methanesulfonamide) disclosed in Patent Literature 1 (Example 9) does not have a diffraction peak at 6.7° to 11.0°, but has diffraction peaks at 6.0°, 11.9°, 17.0°, 17.6° and 19.0° as the diffraction angle (2θ±0.2°), and thus is clearly different from the crystal forms of the present invention.

Said compound [A] (Form A crystal etc.) is useful in the prevention or treatment of various diseases or disease states that involve mineralocorticoid receptor (MR) and/or aldosterone. Examples of such diseases include a cardiovascular disease or a blood-related disease such as essential hypertension; secondary hypertension (renovascular hypertension, fluid retention type hypertension, etc.); pulmonary hypertension; hypotension; abnormal circadian blood pressure; heart failure (acute heart failure, chronic heart failure or congestive heart failure); angina; myocardial infarction; cardiomyopathy; cardiac hypertrophy; myocarditis; myocardial/vascular fibrosis; myocardial ischemia; baroreceptor dysfunction; arrhythmia; tachycardia; cerebrovascular accident (CVA) and a sequel thereof; transient ischemic attack (TIA); cerebral stroke; cerebrovascular dementia; hypertensive encephalopathy; cerebral infarction; cerebral edema; cerebrovascular disorder; peripheral circulatory disturbance including Raynaud's disease and Buerger's disease; intermittent claudication; venous incompetency; arteriosclerosis (coronary arteriosclerosis, cerebral arteriosclerosis, peripheral arteriosclerosis, etc.); vascular hypertrophy; vascular hypertrophy/occlusion after intervention including percutaneous transluminal coronary angioplasty (PTCA); vascular reocclusion/restenosis after bypass graft surgery (CABG etc.); rejection after organ transplant; thrombosis; deep vein thrombosis; occlusive peripheral circulatory disturbance; arteriosclerosis obliterans; thromboangiitis obliterans; thrombocytopenia; polycythemia; multiple organ failure; vascular endothelial dysfunction; renal diseases (renal failure, nephritis, glomerulonephritis, IgA nephropathy, progressive nephropathy, glomerulosclerosis, diabetic nephropathy, thrombotic microangiopathy, dialysis complication, irradiation-induced nephropathy, etc.); vascular purpura; autoimmune hemolytic anemia; disseminated intravascular coagulation (DIC); or multiple myelosis. Particularly, the compound [A] (Form A crystal etc.) is useful as a preventive or therapeutic agent for (1) a cardiovascular disease such as hypertension, heart failure, myocardial infarction, angina, cardiac hypertrophy, myocarditis, myocardial/vascular fibrosis, baroreceptor dysfunction, volume overload or arrhythmia, (2) a disease such as primary/secondary aldosteronism, Addison's disease, Cushing's syndrome or Bartter's syndrome, or (3) a renal disease such as diabetic nephropathy.

The compound [A] (Form A crystal, Form B crystal, etc.) can be orally or parenterally administered alone or as a pharmaceutical composition comprising the compound [A] and a pharmacologically acceptable carrier. Examples of the dosage form of such pharmaceutical composition include, but are not limited to, a conventional solid formulation or a liquid formulation such as a tablet, a granule, a capsule, a powder, an injection, an inhalant or a suppository.

Examples of the pharmacologically acceptable carrier include an excipient, a lubricant, a binder, a disintegrant, a water-soluble polymer, and the like in a solid formulation; and a solvent, a solubilizing agent, an isotonizing agent, a buffer, a suspending agent, and the like in a liquid formulation. Also, in addition to the above carrier, the pharmaceutical composition of the present invention may contain a conventional pharmaceutical additive such as an antioxidant, a preservative, a sweetening agent, an acidulant, a colorant, or a flavoring agent, if necessary.

The dose of the crystal (compound [A]) of the present invention varies depending on administration method, or age, weight, or condition of patient, and preferably 0.001 to 10 mg/kg, particularly 0.01 to 1 mg/kg per day in parenteral administration, and normally 0.01 to 100 mg/kg, particularly 0.1 to 10 mg/kg per day in oral administration.

The starting compound [a] in the present invention can be produced according to, for example, the method disclosed in Patent Literature 1 (i.e., the following Reaction Scheme 1).

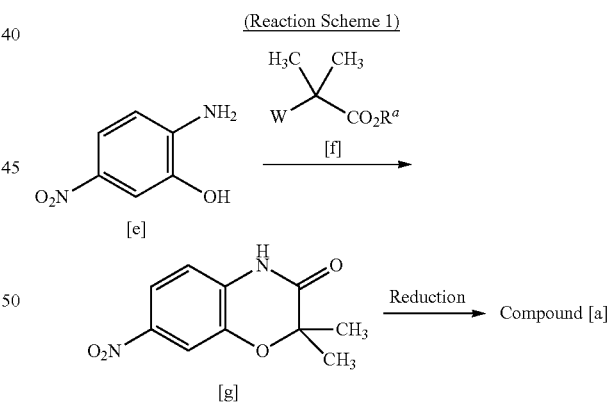

(Reaction Scheme 1)

In the above scheme, $R^a$ is an alkyl group, and W is a halogen atom.

Examples of the halogen atom (W) in the compound [f] include a chlorine atom and a bromine atom, and among them, a bromine atom is preferable. The reaction of the compound [e] with the compound [f] can be carried out in an appropriate solvent (e.g., an ether such as dimethylsulfoxide, an amide such as dimethylformamide, or an ester such as ethyl acetate, etc.), in the presence of a base (e.g., an alkali metal carbonate such as potassium carbonate, etc.), and at room temperature to elevated temperature, preferably 20 to 30° C.

The reduction of the compound [g] (i.e., reduction of the nitro group at 7-position) can be carried out in an appropriate solvent (e.g., an alcohol such as methanol or ethanol, etc.), in the presence of a palladium catalyst such as palladium carbon or palladium hydroxide carbon, under hydrogen atmosphere (or in the presence of ammonium formate), and at 10 to 70° C., preferably 20 to 30° C.

Throughout the present specification, alkyl means a linear or branched $C_{1-6}$ alkyl group, preferably a linear or branched $C_{1-4}$ alkyl group, and alkylene means a linear or branched $C_{1-6}$ alkylene group, preferably a linear or branched $C_{2-6}$ alkylene group.

EXAMPLES

Example 1

(1) Preparation of N-(2,2-dimethyl-3-oxo-3,4-dihydro-2H-1,4-benzoxazin-7-yl)-N-(methylsulfonyl)methanesulfonamide

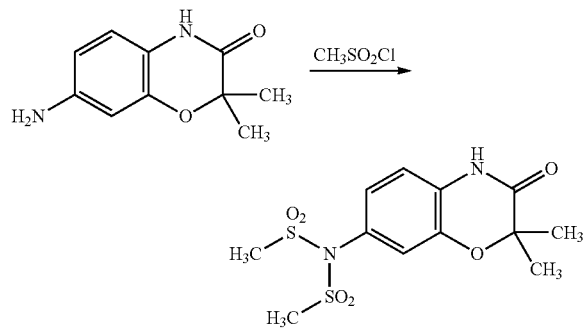

To a suspension of 7-amino-2,2-dimethyl-2H-1,4-benzoxazin-3-(4H)-one (150 g) in acetonitrile (1500 mL) was added dropwise triethylamine (79 g) at 40° C., then to the mixture was added dropwise methanesulfonyl chloride (89.4 g) (internal temperature: 39 to 50° C.), and stirred at the same temperature for 20 minutes. To the reaction mixture were successively added dropwise triethylamine (79 g) and methanesulfonyl chloride (89.4 g) (internal temperature: 42 to 50° C.), and then stirred at the same temperature for 25 minutes. To the reaction mixture were successively added dropwise additional triethylamine (39.5 g) and methanesulfonyl chloride (44.7 g) (internal temperature: 42 to 47° C.), and stirred at 40° C. for 4 hours. To the reaction mixture was added dropwise water (1500 mL), the mixture was stirred at 40° C. for 1 hour, then cooled to 25° C., and then stirred for 30 minutes. The precipitated crystals were collected by filtration, successively washed with acetonitrile/water (1:1, 300 mL) and water (750 mL), and dried to obtain the title compound (235.1 g) as white crystals (yield: 87%, purity: 99%).

MS: ESI-MS m/Z: 349 [M+H]$^+$ $^1$H-NMR (CDCl$_3$): δ 1.54 (6H, s), 2.20 (1H, brs), 3.41 (6H, s), 6.85 (1H, d), 6.95 (1H, d), 6.96 (1H, s)

(2) Preparation of N-[4-(4-fluorophenyl)-2,2-dimethyl-3-oxo-3,4-dihydro-2H-1,4-benzoxazin-7-yl]-N-(methylsulfonyl)methanesulfonamide

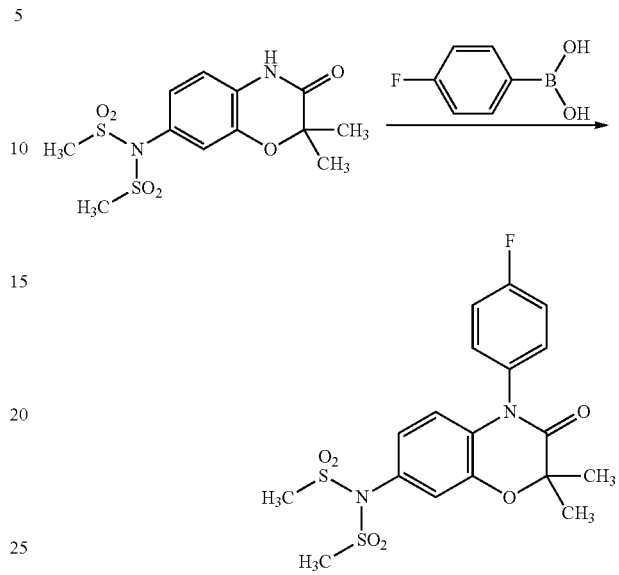

The compound (300.0 g) obtained in the above step (1), 4-fluorophenylboronic acid (210.8 g), 4-dimethylaminopyridine (21.0 g), tributylamine (127.7 g) and copper(II) acetate monohydrate (17.2 g) were added to dimethylsulfoxide (2250 mL), and the mixture was stirred at 20° C. for 25 hours under blowing air (150 mL/min) thereto. To the reaction mixture was added methanol (1500 mL), and then to the mixture was added dropwise hydrochloric acid/water (179 g/2130 mL) at about 30° C. or lower. After the mixture was stirred for 1 hour, the precipitated crystals were successively washed with water (3000 mL) and methanol (1500 mL), and then dried to obtain the title compound (350.5 g) as white crystals (yield: 92%, purity: 94%).

MS: ESI-MS m/Z: 443 [M+H]$^+$ $^1$H-NMR (CDCl$_3$): δ 1.63 (6H, s), 3.39 (6H, s), 6.40 (1H, d), 6.84 (1H, dd), 7.03 (1H, d), 7.20-7.25 (4H, m)

(3) Preparation of N-[4-(4-fluorophenyl)-2,2-dimethyl-3-oxo-3,4-dihydro-2H-1,4-benzoxazin-7-yl]methanesulfonamide

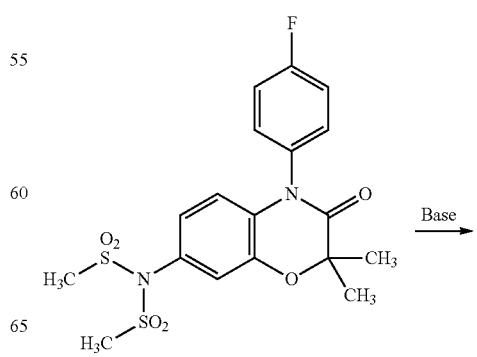

-continued

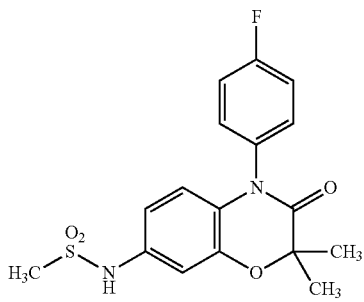

The compound (10 g) obtained in the above step (2) was dissolved in dimethylsulfoxide (60 mL), and the solution was filtered to remove insoluble materials. After the filtrate and the washings were combined, an aqueous solution of anhydrous potassium carbonate (9.4 g/10 mL) was added dropwise thereto at 30° C. or lower, and the mixture was stirred at the same temperature for 25 hours. To the reaction mixture was added dropwise concentrated hydrochloric acid/water (4.7 g/90 mL) at 30° C. or lower, and the mixture was stirred for 30 minutes. The precipitated crystals were collected by filtration, and successively washed with water (90 mL) and ethanol (20 mL) to obtain the title compound (9.1 g) as white crystals (Form B crystals). The crystals were suspended in ethanol (100 mL), the suspension was heated under reflux for 2 hours, and then cooled to room temperature. The precipitated crystals were collected by filtration, and dried under reduced pressure at 50° C. to obtain the title compound (7.1 g) as crystals (Form A crystals) (yield: 86%, purity: 99%).

M.p.: 240° C.

MS: ESI-MS m/Z: 365 [M+H]$^+$ $^1$H-NMR (DMSO-d$_6$): δ 1.51 (6H, s), 2.95 (3H, s), 6.25 (1H, d), 6.75 (1H, dd), 6.90 (1H, d), 7.35-7.41 (4H, m), 9.69 (1H, brs)

Example 2

Preparation of N-[4-(4-fluorophenyl)-2,2-dimethyl-3-oxo-3,4-dihydro-2H-1,4-benzoxazin-7-yl]methanesulfonamide

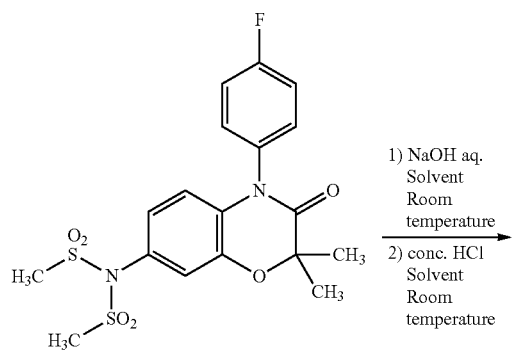

-continued

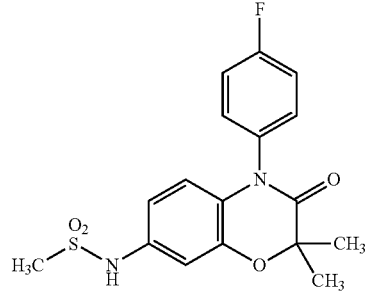

To a suspension of N-[4-(4-fluorophenyl)-2,2-dimethyl-3-oxo-3,4-dihydro-2H-1,4-benzoxazin-7-yl]-N-(methylsulfonyl)methanesulfonamide (1 g) in acetone (3 mL) was added dropwise an aqueous sodium hydroxide solution (0.18 g/3 mL) at 25° C., and the mixture was stirred at the same temperature for 90 minutes. To the reaction mixture was added dropwise concentrated hydrochloric acid/acetone/water (0.24 g/0.5 mL/0.35 mL) at 25° C., and the mixture was stirred for 2 hours. The precipitated crystals were collected by filtration, washed with a solution of acetone/water (1:1.6 mL), and then dried under reduced pressure at 50° C. to obtain the title compound (0.79 g) as Form A crystals (yield: 95%, purity: 100%).

M.p.: 240° C.

Example 3

Preparation of N-[4-(4-fluorophenyl)-2,2-dimethyl-3-oxo-3,4-dihydro-2H-1,4-benzoxazin-7-yl]methanesulfonamide

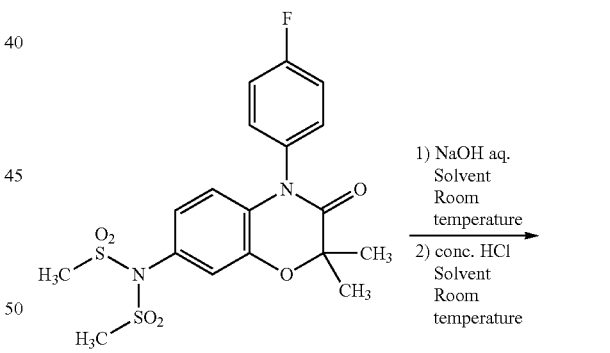

To a suspension of N-[4-(4-fluorophenyl)-2,2-dimethyl-3-oxo-3,4-dihydro-2H-1,4-benzoxazin-7-yl]-N-(methylsulfonyl)methanesulfonamide (1 g) in dimethylsulfoxide (3 mL) was added dropwise an aqueous sodium hydroxide solution (0.18 g/3 mL) at 25° C., then dimethylsulfoxide/water (1:1.2 mL) was added thereto, and the mixture was stirred overnight at the same temperature. To the reaction mixture was added dropwise concentrated hydrochloric acid/dimethylsulfoxide/water (0.24 g/0.5 mL/0.35 mL) at 25° C., and the mixture was stirred for 5 hours. The precipitated crystals were collected by filtration, successively washed with a solution of dimethylsulfoxide/water (1:1.6 mL) and water (10 mL), and then dried under reduced pressure at 50° C. to obtain the title compound (0.81 g) as Form A crystals (yield: 98%, purity: 100%).

M.p.: 240° C.

Example 4

Preparation of N-[4-(4-fluorophenyl)-2,2-dimethyl-3-oxo-3,4-dihydro-2H-1,4-benzoxazin-7-yl]methanesulfonamide

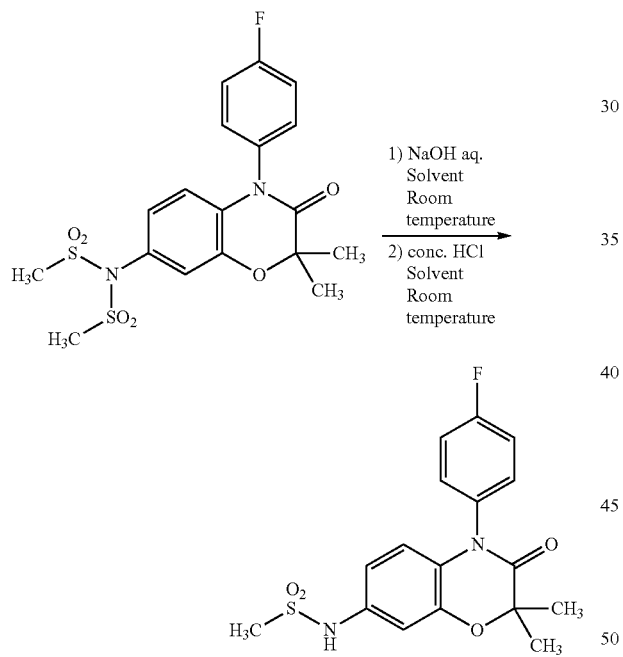

To a suspension of N-[4-(4-fluorophenyl)-2,2-dimethyl-3-oxo-3,4-dihydro-2H-1,4-benzoxazin-7-yl]-N-(methylsulfonyl)methanesulfonamide (1 g) in ethanol (3 mL) was added dropwise an aqueous sodium hydroxide solution (0.18 g/3 mL) at 25° C., then ethanol/water (1:1.2 mL) was added thereto, and the mixture was stirred overnight at the same temperature. To the reaction mixture was added dropwise concentrated hydrochloric acid/ethanol/water (0.24 g/0.5 mL/0.35 mL) at 25° C., and the mixture was stirred for 1 hour. The precipitated crystals were collected by filtration, washed with a solution of ethanol/water (1:1.6 mL), and then dried under reduced pressure at 50° C. to obtain the title compound (0.80 g) as Form B crystals (yield: 98%, purity: 95%).

Example 5

Preparation of N-[4-(4-fluorophenyl)-2,2-dimethyl-3-oxo-3,4-dihydro-2H-1,4-benzoxazin-7-yl]methanesulfonamide

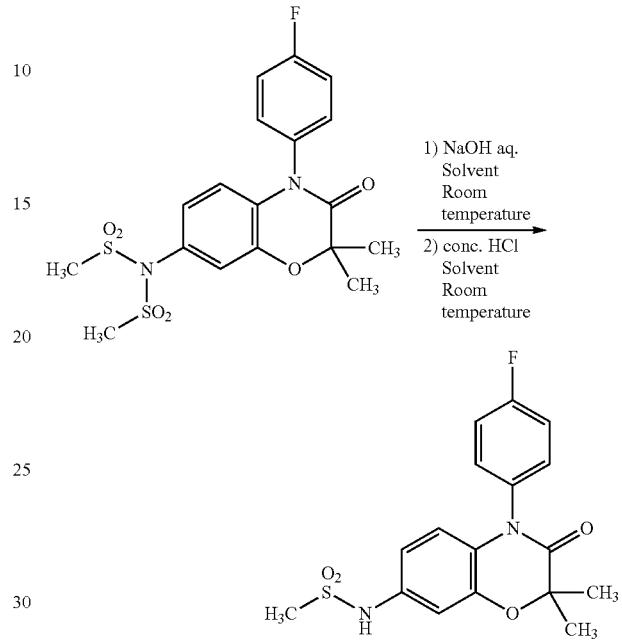

To a suspension of N-[4-(4-fluorophenyl)-2,2-dimethyl-3-oxo-3,4-dihydro-2H-1,4-benzoxazin-7-yl]-N-(methylsulfonyl)methanesulfonamide (1 g) in isopropanol (3 mL) was added dropwise an aqueous sodium hydroxide solution (0.18 g/3 mL) at 25° C., then isopropanol/water (1:1.2 mL) was added thereto, and the mixture was stirred overnight at the same temperature. To the reaction mixture was added dropwise concentrated hydrochloric acid/isopropanol/water (0.24 g/0.5 mL/0.35 mL) at 25° C., and the mixture was stirred for 1 hour. The precipitated crystals were collected by filtration, washed with a solution of isopropanol/water (1:1.6 mL), and then dried under reduced pressure at 50° C. to obtain the title compound (0.78 g) as Form D crystals (yield: 94%, purity: 99%).

Example 6

Preparation of N-[4-(4-fluorophenyl)-2,2-dimethyl-3-oxo-3,4-dihydro-2H-1,4-benzoxazin-7-yl]-N-(methylsulfonyl)methanesulfonamide

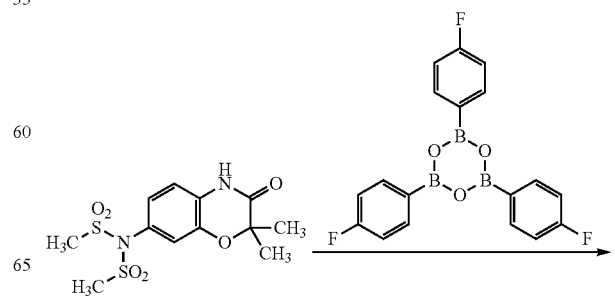

-continued

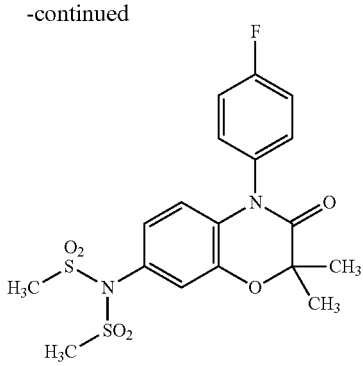

N-(2,2-dimethyl-3-oxo-3,4-dihydro-2H-1,4-benzoxazin-7-yl)-N-(methylsulfonyl)methanesulfonamide (200 g), tris(4-fluorophenyl)boroxine (140.5 g), 4-dimethylaminopyridine (14.0 g), tributylamine (85.1 g) and copper(II) acetate monohydrate (11.5 g) were added to dimethylsulfoxide (1500 mL), and the mixture was stirred at 20° C. for 72 hours under blowing air (850 mL/min) dehydrated with silica gel thereto. To the reaction mixture was added dropwise an aqueous hydrochloric acid solution (concentrated hydrochloric acid (119.7 g)/water (1422 mL)) at 30° C. or lower, then methanol (1000 mL) was added thereto, and the mixture was stirred at 20° C. for 2 hours. The precipitated crystals were collected by filtration, successively washed with water (2000 mL) and methanol (1000 mL), and then suspended in methanol (2000 mL). The suspension was heated under reflux for 1.5 hours, then cooled to 20° C., and stirred at the same temperature for 30 minutes. The precipitated crystals were collected by filtration, washed with methanol (1000 mL), and then dried to obtain the title compound (226.2 g) (yield: 89%, purity: 99%).

Example 7

Preparation of N-[4-(4-fluorophenyl)-2,2-dimethyl-3-oxo-3,4-dihydro-2H-1,4-benzoxazin-7-yl]-N-(methylsulfonyl)methanesulfonamide

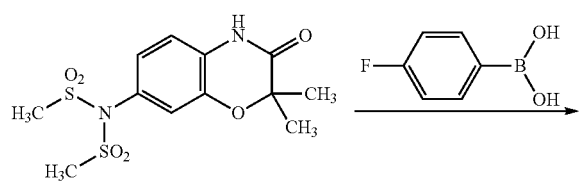

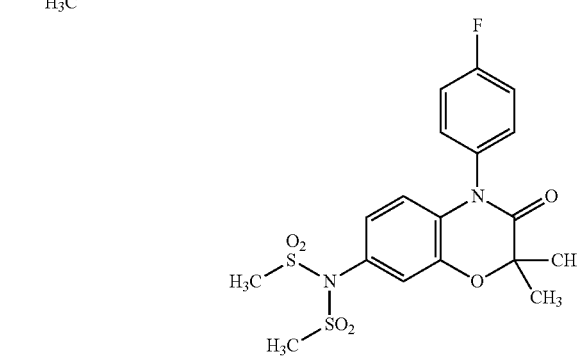

N-(2,2-dimethyl-3-oxo-3,4-dihydro-2H-1,4-benzoxazin-7-yl)-N-(methylsulfonyl)methanesulfonamide (7.50 g), 4-fluorophenylboronic acid (5.27 g), 4-dimethylaminopyridine (0.53 g), tributylamine (3.20 g) and copper(II) acetate monohydrate (0.43 g) were added to dimethylsulfoxide (56 mL), and the mixture was stirred at 20° C. for 26 hours under blowing air (7 to 10 mL/min) thereto. The reaction mixture was added dropwise to a mixed solution of dimethylsulfoxide/concentrated hydrochloric acid/water (19 mL/4.5 g/34 mL) at about 15° C., and washed with dimethylsulfoxide (7.5 mL). The mixture was stirred at 10° C. for 3 hours, then the precipitated crystals were successively washed with dimethylsulfoxide/water (12 mL/3 mL) and water (75 mL), and then dried to obtain the title compound (9.09 g) as white crystals (yield: 95%, purity: 92%).

Example 8

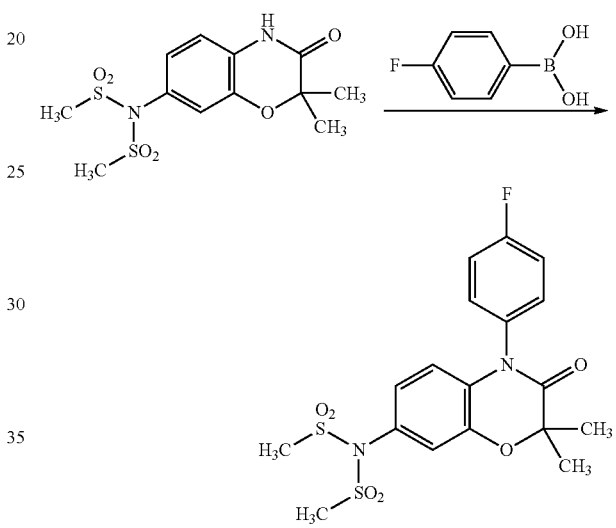

N-(2,2-dimethyl-3-oxo-3,4-dihydro-2H-1,4-benzoxazin-7-yl)-N-(methylsulfonyl)methanesulfonamide (40.0 g), 4-fluorophenylboronic acid (28.1 g), 1-methylimidazole (0.9 g), tributylamine (27.3 mL) and copper(II) acetate (2.1 g) were added to dimethylsulfoxide (300 mL), and the mixture was stirred at 20° C. for 34 hours under nitrogen flow (120 mL/min) and blowing air (40 mL/min) thereto. The reaction mixture was added dropwise to a mixed solution of dimethylsulfoxide/concentrated hydrochloric acid/water (110.0 g/24.0 g/180.0 g) at about 15° C., and washed with dimethylsulfoxide (44.0 g). The mixture was stirred at 10° C. for 2 hours, then the precipitated crystals were successively washed with dimethylsulfoxide/water (70.4 g/16.0 g) and water (400.0 g), and then dried to obtain the title compound (47.8 g) as white crystals (yield: 94%, purity: 94%).

Example 9

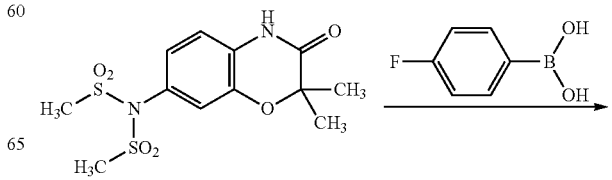

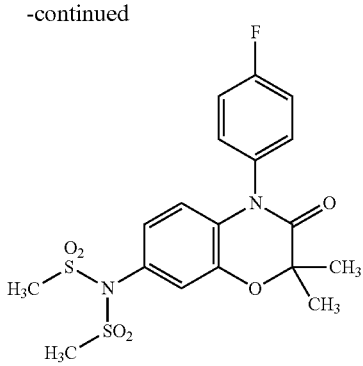

N-(2,2-dimethyl-3-oxo-3,4-dihydro-2H-1,4-benzoxazin-7-yl)-N-(methylsulfonyl)methanesulfonamide (40.0 g), 4-fluorophenylboronic acid (28.1 g), tributylamine (21.8 mL) and copper(II) acetate (12.5 g) were added to dimethylsulfoxide (300 mL), and the mixture was stirred at 40° C. for 71 hours under nitrogen flow (120 ml/min) and blowing air (40 mL/min) thereto. The reaction mixture was added dropwise to a mixed solution of dimethylsulfoxide/concentrated hydrochloric acid/water (110.0 g/24.0 g/180.0 g) at about 15° C., and washed with dimethylsulfoxide (44.0 g). After the mixture was stirred at 10° C. for 2 hours, the precipitated crystals were successively washed with dimethylsulfoxide/water (70.4 g/16.0 g) and water (400.0 g), and then dried to obtain the title compound (47.6 g) as white crystals (yield: 94%, purity: 91%).

Example 10

Preparation of N-[4-(4-fluorophenyl)-2,2-dimethyl-3-oxo-3,4-dihydro-2H-1,4-benzoxazin-7-yl]methanesulfonamide

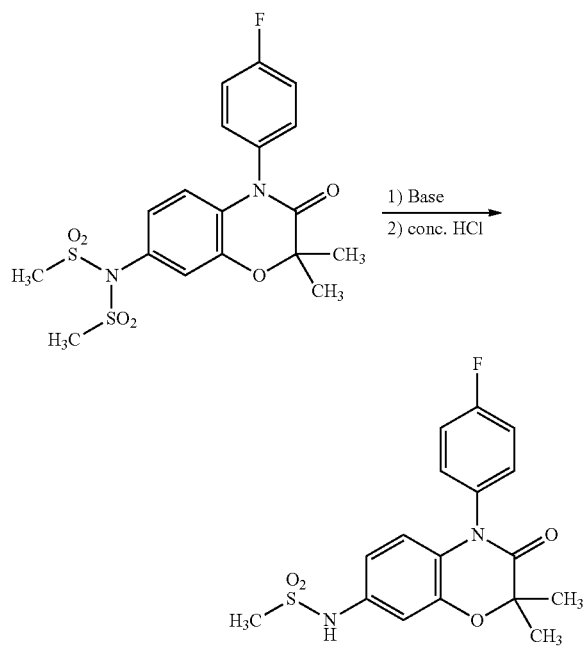

N-[4-(4-fluorophenyl)-2,2-dimethyl-3-oxo-3,4-dihydro-2H-1,4-benzoxazin-7-yl]-N-(methylsulfonyl)methanesulfonamide (8.5 g) was dissolved in dimethylsulfoxide (51 mL), a solution of potassium carbonate/water (7.98 g/8.5 mL) was added dropwise thereto at 25° C., and the mixture was stirred at the same temperature for 23 hours. To the reaction mixture was added dropwise concentrated hydrochloric acid/water (4.0 g/76.5 mL) at 30° C. or lower, then cooled to 20° C., and the mixture was stirred for 90 minutes. The precipitated crystals were collected by filtration, washed with water (76.5 mL), and then dried to obtain the title compound (6.40 g) as white crystals (Form B crystals). Subsequently, said crystals (6 g) were added to dimethylsulfoxide (21 mL), dissolved at about 50° C., then activated carbon (120 mg) and dimethylsulfoxide (3 mL) were added thereto, and stirred for 1 hour. After the mixture was filtered, to the filtrate at about 50° C. was added dropwise purified water (9 mL), and then stirred at the same temperature for 30 minutes. The mixture was cooled to 20° C., stirred for 1 hour, then the precipitated crystals were collected by filtration, and successively washed with purified water (54 mL) and ethanol (12 mL). The obtained crystals (6.57 g) were suspended in ethanol (30 mL), the suspension was heated under reflux for 2 hours, then cooled to 20° C., and stirred for 1 hour. The precipitated crystals were collected by filtration, and dried under reduced pressure at 50° C. to obtain the title compound (5.48 g) as crystals (Form A crystals) (yield: 83%, purity: 100%).

Experimental Example 1

X-ray crystallographic analysis under the following conditions was carried out on each of the crystals (Form A crystal, Form B crystal and Form D crystal) of the target compound obtained in the above each EXAMPLE, and the crystal (Form C crystal) obtained by the experiment for screening crystal forms. As a result of the analysis, it was confirmed that the Form A crystal (i.e., crystal obtained in EXAMPLES 1, 2 and 3), the Form B crystal (i.e., crystal obtained in EXAMPLE 4), and the Form C crystal were novel crystal forms each having a clearly different XRD pattern from the crystal form of the compound [A] disclosed in Patent Literature 1 (Example 9). Meanwhile, by the analyses such as X-ray crystallographic diffraction and melting point, it was confirmed that the Form D crystal (i.e., crystal obtained in EXAMPLE 5) was the same as the crystal form of the compound [A] (i.e., compound obtained in REFERENCE EXAMPLE 2) prepared according to the method disclosed in Patent Literature 1 (Example 9). The XRD diffraction pattern of each crystal form obtained in the EXAMPLES of the present specification is shown in the following FIG. 1 to FIG. 4. Also, the diffraction angle (2θ) values of the diffraction peaks observed in each crystal form are shown in Table 1 to Table 4.

Figure 2:
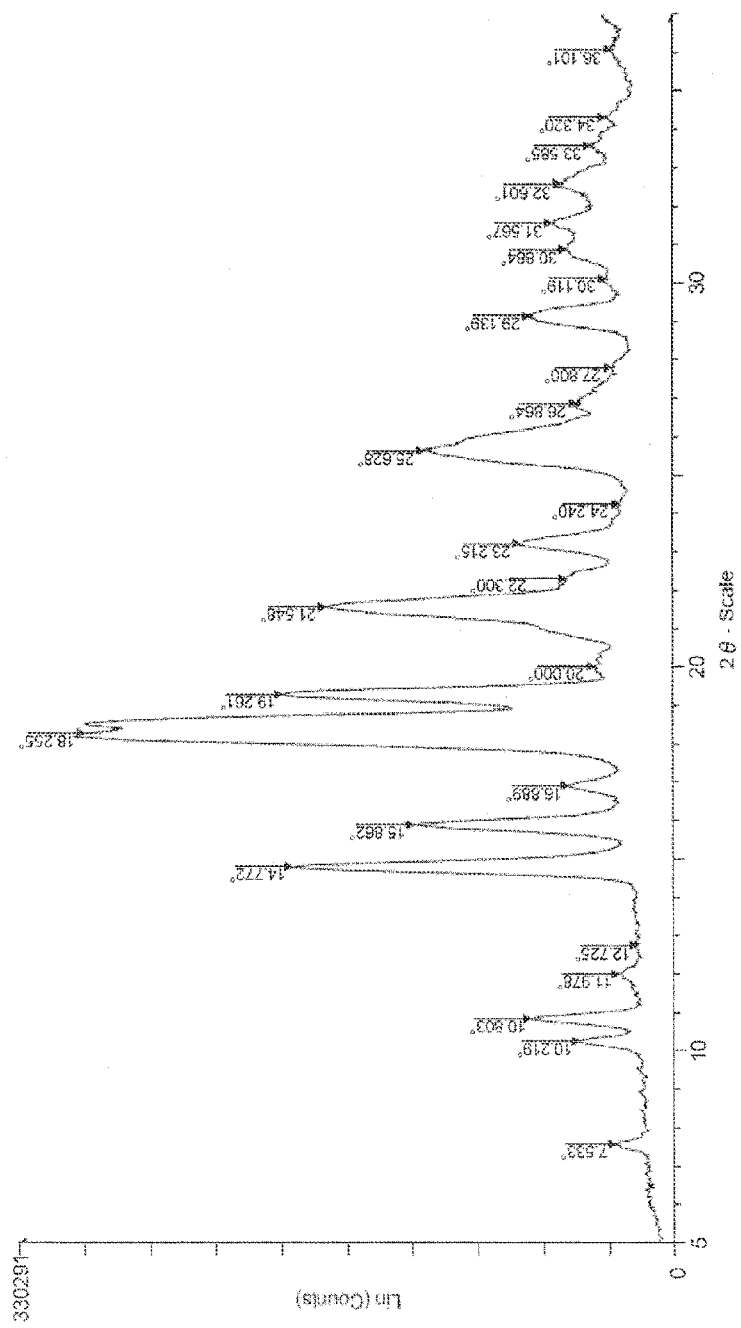
FIG. 2 shows the X-ray powder diffraction pattern of the Form B crystal of the compound [A].
Figure 3:
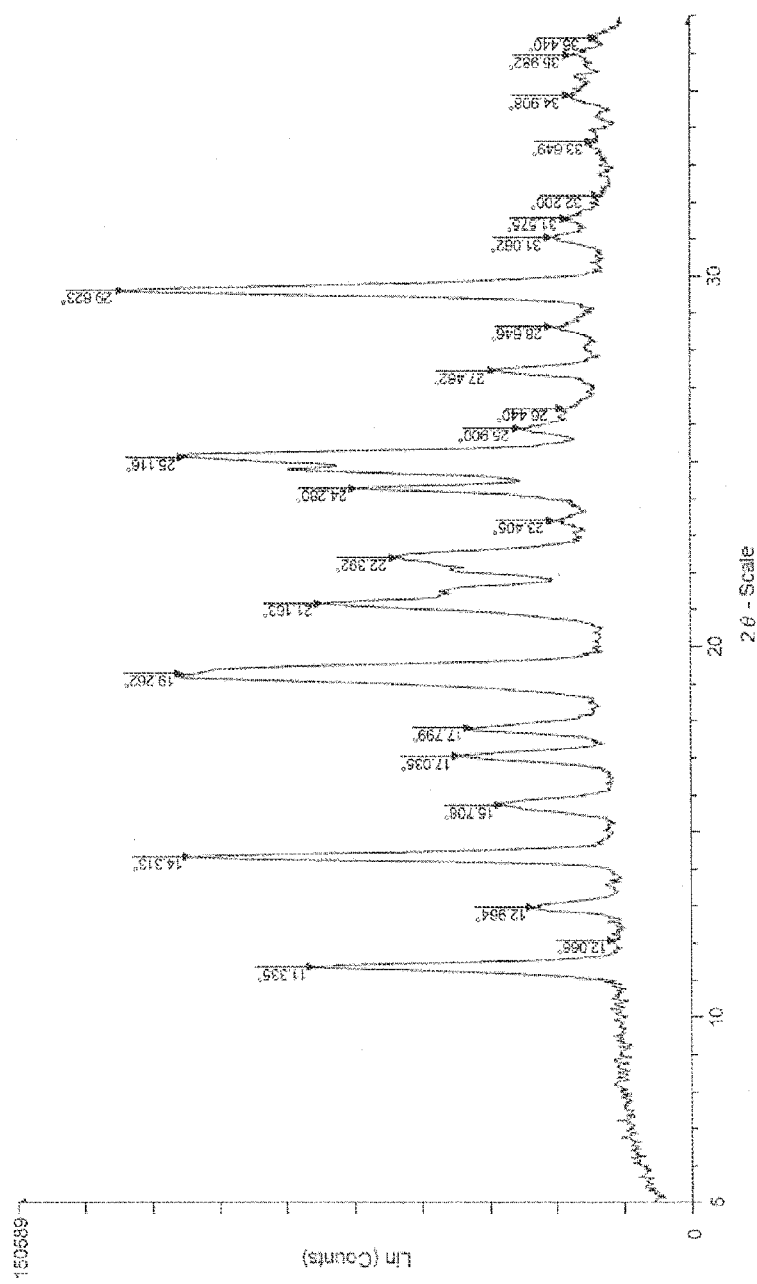
FIG. 3 shows the X-ray powder diffraction pattern of the Form C crystal of the compound [A].
Figure 4:
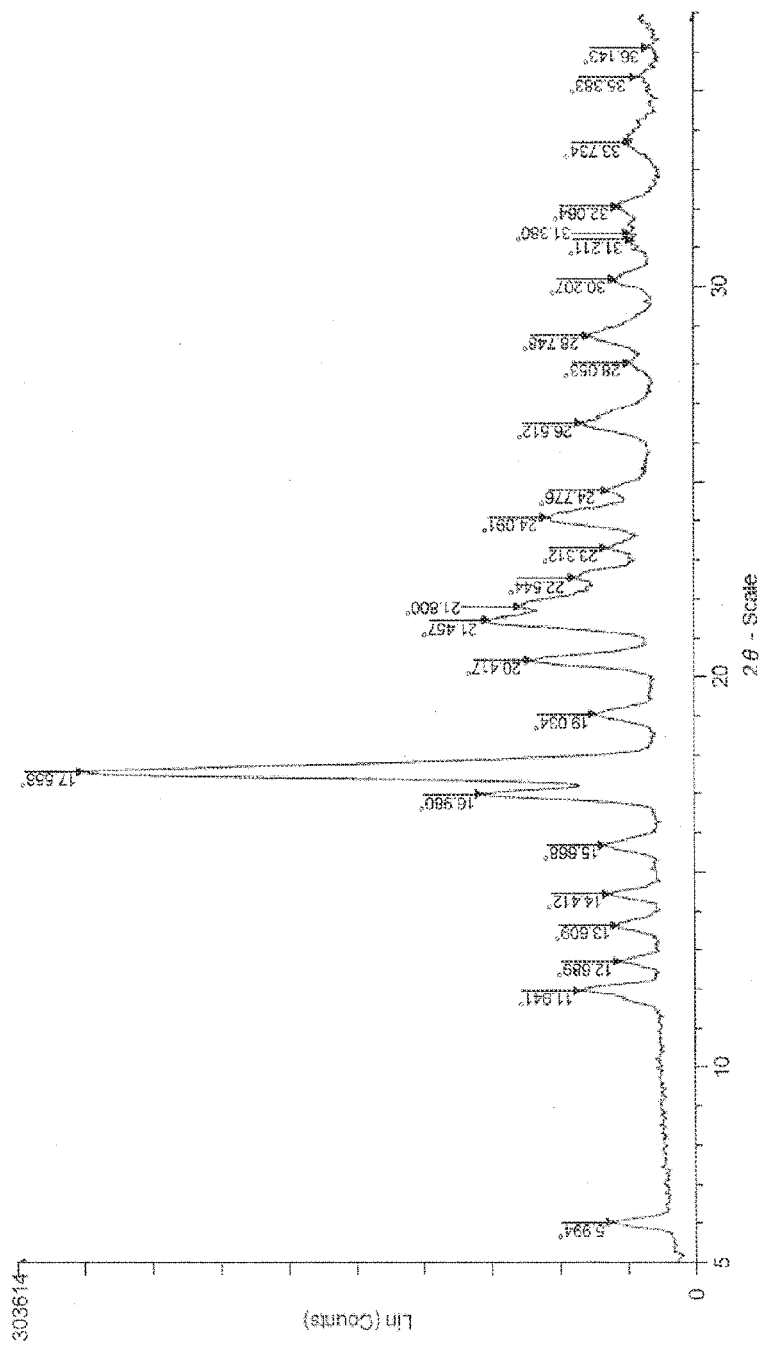
FIG. 4 shows the X-ray powder diffraction pattern of the Form D crystal of the compound [A].

Device name: DISCOVER with GADDS CS (made by BRUKER CORPORATION)
X-ray source: CuKα
Tube voltage: 40 kV
Tube current: 40 mA
Measurement range (2θ): 5 to 370
Detector: Multiwire two-dimensional PSPC FIG. 1 shows the X-ray powder diffraction pattern of the Form A crystal of the compound [A].
FIG. 2 shows the X-ray powder diffraction pattern of the Form B crystal of the compound [A].
FIG. 3 shows the X-ray powder diffraction pattern of the Form C crystal of the compound [A].
FIG. 4 shows the X-ray powder diffraction pattern of the Form D crystal of the compound [A].

Table 1 shows the diffraction angles (2θ) of the Form A crystal of the compound [A].

Table 2 shows the diffraction angles (2θ) of the Form B crystal of the compound [A].

Table 3 shows the diffraction angles (2θ) of the Form C crystal of the compound [A].

Table 4 shows the diffraction angles (2θ) of the Form D crystal of the compound [A].

TABLE 1

| Peak No. | 2θ (°) |
| --- | --- |
| 1 | 6.4 |
| 2 | 7.4 |
| 3 | 8.3 |
| 4 | 9.7 |
| 5 | 10.2 |
| 6 | 11.2 |
| 7 | 13.0 |
| 8 | 13.6 |
| 9 | 14.2 |
| 10 | 16.0 |
| 11 | 16.4 |
| 12 | 17.3 |
| 13 | 18.1 |
| 14 | 20.2 |
| 15 | 20.9 |
| 16 | 21.3 |
| 17 | 22.4 |
| 18 | 23.7 |
| 19 | 25.1 |
| 20 | 25.7 |
| 21 | 27.3 |
| 22 | 28.1 |
| 23 | 28.8 |
| 24 | 29.5 |
| 25 | 30.3 |
| 26 | 30.8 |
| 27 | 31.4 |
| 28 | 33.2 |
| 29 | 33.9 |
| 30 | 34.5 |
| 31 | 35.2 |
| 32 | 36.6 |

TABLE 2

| Peak No. | 2θ (°) |
| --- | --- |
| 1 | 7.5 |
| 2 | 10.2 |
| 3 | 10.8 |
| 4 | 12.0 |
| 5 | 12.7 |
| 6 | 14.8 |
| 7 | 15.9 |
| 8 | 16.9 |
| 9 | 18.3 |
| 10 | 19.3 |
| 11 | 20.0 |
| 12 | 21.5 |
| 13 | 22.3 |
| 14 | 23.2 |
| 15 | 24.2 |
| 16 | 25.6 |
| 17 | 26.9 |
| 18 | 27.8 |
| 19 | 29.1 |
| 20 | 30.1 |
| 21 | 30.9 |
| 22 | 31.6 |
| 23 | 32.6 |
| 24 | 33.6 |
| 25 | 34.3 |
| 26 | 36.1 |

TABLE 3

| Peak No. | 2θ (°) |
| --- | --- |
| 1 | 11.3 |
| 2 | 12.1 |
| 3 | 13.0 |
| 4 | 14.3 |
| 5 | 15.7 |
| 6 | 17.0 |
| 7 | 17.8 |
| 8 | 19.3 |
| 9 | 21.2 |
| 10 | 22.4 |
| 11 | 23.4 |
| 12 | 24.3 |
| 13 | 25.1 |
| 14 | 25.9 |
| 15 | 26.4 |
| 16 | 27.5 |
| 17 | 28.6 |
| 18 | 29.6 |
| 19 | 31.1 |
| 20 | 31.6 |
| 21 | 32.2 |
| 22 | 33.6 |
| 23 | 34.9 |
| 24 | 36.0 |
| 25 | 36.4 |

TABLE 4

| Peak No. | 2θ (°) |
| --- | --- |
| 1 | 6.0 |
| 2 | 11.9 |
| 3 | 12.7 |
| 4 | 13.6 |
| 5 | 14.4 |
| 6 | 15.7 |
| 7 | 17.0 |
| 8 | 17.6 |
| 9 | 19.0 |
| 10 | 20.4 |
| 11 | 21.5 |
| 12 | 21.8 |
| 13 | 22.5 |
| 14 | 23.3 |
| 15 | 24.1 |
| 16 | 24.8 |
| 17 | 26.5 |
| 18 | 28.1 |
| 19 | 28.7 |
| 20 | 30.2 |
| 21 | 31.2 |
| 22 | 31.4 |
| 23 | 32.1 |
| 24 | 33.7 |
| 25 | 35.4 |
| 26 | 36.1 |

The Form A crystal (or Form B crystal) and the Form D crystal are clearly different from each other in that while the former crystal has at least one diffraction peak at 6.7° to 11.0° as the diffraction angle (2θ±0.2°), the latter crystal does not have any diffraction peak at 6.7° to 11.0° as the diffraction angle (2θ±0.2°) in their XRD patterns (FIG. 1, FIG. 2, FIG. 4, Table 1, Table 2 and Table 4). This fact teaches that the Form A crystal and the Form D crystal have different crystal structures from each other. Meanwhile, it was confirmed that the Form D crystal has the same crystal form as the crystal of the compound [A] prepared according to the method disclosed in Patent Literature 1 (WO2007/089034, Example 9) (see REFERENCE EXAMPLE 2 described below).

Reference Example 1

(1) Preparation of 2,2-dimethyl-7-nitro-2H-1,4-benzoxazin-3(4H)-one

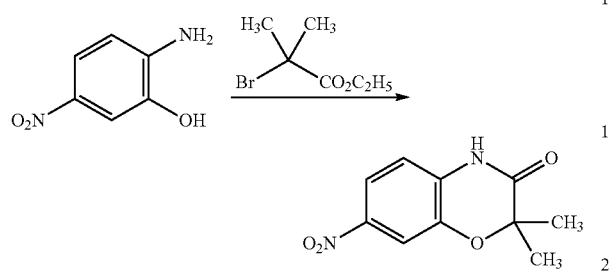

To a solution of 2-amino-5-nitrophenol (200 g) in dimethylsulfoxide (1000 mL) was added anhydrous potassium carbonate (269 g) under stirring at 30° C. or lower, then to the mixture was added ethyl 2-bromo-2-methylpropionate (278.4 g) at 30° C. or lower, and the mixture was stirred at 26° C. for 24 hours. To the reaction mixture was added water (2000 mL) at 40° C. or lower, and then stirred at room temperature for 3 hours. The reaction product was collected by filtration, and successively washed with dimethylsulfoxide/water (2:1, 800 mL) and water (3200 mL) to obtain the title compound (348.6 g) as a yellow solid (wet material) (yield: 121%, purity: 96%).

MS: ESI-MS m/Z: 223 [M+H]$^+$ $^1$H-NMR (CDCl$_3$): δ 1.59 (6H, s), 6.95 (1H, d), 7.87 (1H, d), 7.92 (1H, dd), 9.38 (1H, brs)

(2) Preparation of 7-amino-2,2-dimethyl-2H-1,4-benzoxazin-3(4H)-one

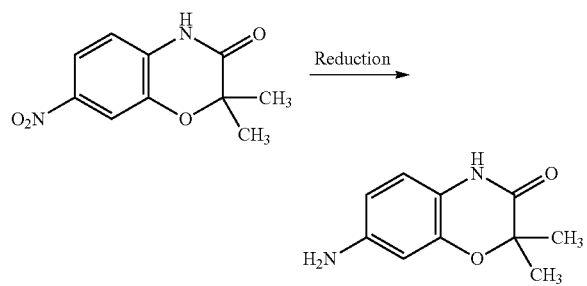

A mixture of the compound (wet material: 384.6 g) obtained in the above step (1), methanol (2880 mL), and 20% palladium hydroxide carbon (13.8 g) was stirred under hydrogen pressure (0.1 MPa) at 40° C. until hydrogen absorption terminated (about 4 hours). The reaction mixture was filtered, and the unfiltered residue was washed with methanol (300 mL). The filtrate and the washings were combined, then concentrated under reduced pressure at 50° C. or lower, to the residue were added methanol (288 mL) and water (1440 mL), and the mixture was stirred at 50° C. for about 1 hour. The mixture was cooled to 25° C., then stirred for 30 minutes, the precipitated crystals were collected by filtration, washed with water (1440 mL), and then dried to obtain the title compound (163.94 g) as red-brown crystals (yield: 66%, purity: 100%).

MS: ESI-MS m/Z: 193 [M+H]

$^1$H-NMR (CDCl$_3$): δ 1.51 (6H, s), 3.56 (2H, brs), 6.29 (1H, dd), 6.32, 6.33 (1H, m), 6.59 (1H, d), 8.34 (1H, brs)

Reference Example 2

Preparation of N-[4-(4-fluorophenyl)-2,2-dimethyl-3-oxo-3,4-dihydro-2H-1,4-benzoxazin-7-yl]methanesulfonamide (Form D Crystal)

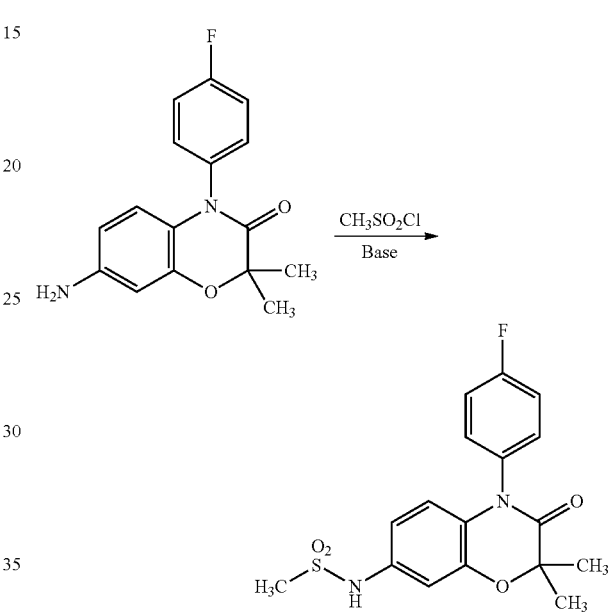

The compound [A] was prepared by the following steps according to the method disclosed in Patent Literature 1.

To a solution of 7-amino-4-(4-fluorophenyl)-2,2-dimethyl-2H-1,4-benzoxazin-3(4H)-one (11.0 g) in chloroform (200 mL) were added dropwise methanesulfonyl chloride (4.46 mL) and pyridine (6.21 mL) under ice cooling, and then the mixture was stirred at room temperature for 17 hours. To the reaction mixture was poured an aqueous saturated sodium hydrogen carbonate solution, and the mixture was extracted with chloroform. The organic layer was successively washed with water, 10% hydrochloric acid and a saturated saline, then dried over sodium sulfate, and concentrated under reduced pressure. The obtained residue was suspended in ethyl acetate, and then the precipitated materials were collected by filtration, and washed with ethyl acetate to obtain the title compound (10.2 g) as a pale pink powder.

APCI-MS m/z: 365 [M+H]$^+$

M.p.: 233° C.

$^1$H-NMR (CDCl$_3$): δ 1.60 (6H, s), 3.01 (3H, s), 6.32 (1H, d), 6.44 (1H, brs), 6.69 (1H, dd), 6.95 (1H, d), 7.20-7.22 (4H, m)

INDUSTRIAL APPLICABILITY

By using the method of the present invention, the 1,4-benzoxazine compound [A] useful as a medicine can be prepared in a high yield. Furthermore, the method of the present invention can use an intermediate having lower mutagenicity, and thus is also characterized by lower safety and health risks and can be an industrially advantageous method for producing the 1,4-benzoxazine compound [A].

Also, the crystals (Form A crystal etc.) of the compound [A] of the present invention are useful as a preventive or therapeutic agent for diseases such as hypertension or a renal disease (diabetic nephropathy etc.).

The invention claimed is:

1. A method for producing a compound of the following formula [c]:

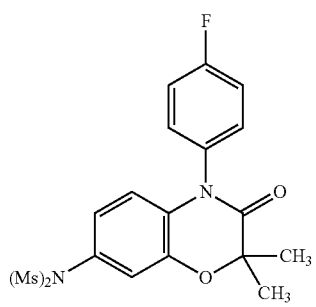

wherein Ms is a methanesulfonyl group,
which comprises the following steps of:
(step a) reacting a compound of the following formula [a]:

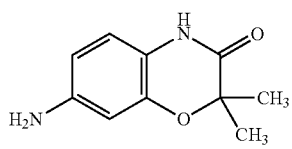

with methanesulfonyl halide in the presence of a base to produce a compound of the following formula [b]:

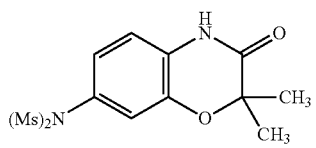

wherein the symbol is the same as defined above, and
(step b) reacting said compound [b] with a boronic acid compound of the following formula [d]:

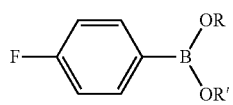

wherein R and R' are the same or different and each of them is a hydrogen atom or an alkyl group, or both of them combine together to form an alkylene group, or an equivalent thereof, in the presence of a copper catalyst, in the presence or absence of a base, and in the presence or absence of a ligand selected from the group consisting of a pyridine, an imidazole, 1,4-diazabicyclo[2.2.2]octane, pyrazine, and mixtures thereof.

2. The method according to claim 1, characterized in that
the step a is carried out in a solvent selected from the group consisting of acetonitrile, methyl ethyl ketone, ethyl acetate, tetrahydrofuran and acetone, and in the presence of a base selected from the group consisting of triethylamine, tetramethylethylenediamine and 1,8-diazabicyclo[5.4.0]undec-7-ene, and the step b is carried out in a solvent selected from the group consisting of dimethylsulfoxide and N,N-dimethylacetamide, in the presence of a copper catalyst selected from the group consisting of copper acetate, copper halide, copper nitrate and a copper salt of trifluoromethanesulfonic acid, in the presence or absence of one or more bases selected from the group consisting of triethylamine, diisopropylethylamine, tributylamine, tripropylamine, trioctylamine, dimethylbenzylamine, 1,8-diazabicyclo[5.4.0]undec-7-ene, N-ethylmorpholine, N-methylmorpholine, sodium hydrogen carbonate and an aqueous ammonia, in the presence or absence of one or more ligands selected from the group consisting of dimethylaminopyridine, 2-aminopyridine, 4-methylpyridine, 2,6-dimethylpyridine, 3,5-dimethylpyridine, pyridine, N-methylimidazole, N-butylimidazole and pyrazine, and under oxygen supply to the reaction system.

3. A method for producing a compound of the following formula [c]:

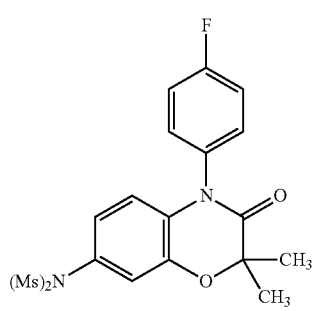

wherein Ms is a methanesulfonyl group,
which comprises the step of reacting a compound of the following formula [b]:

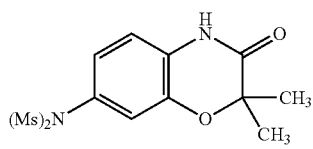

wherein the symbol is the same as defined above,
with a boronic acid compound of the following formula [d]:

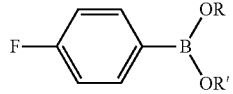
[d]

wherein R and R' are the same or different and each of them is a hydrogen atom or an alkyl group, or both of them combine together to form an alkylene group,
or an equivalent thereof, in the presence of a copper catalyst, in the presence or absence of a base, and in the presence or absence of a ligand selected from the group consisting of a pyridine, an imidazole, 1,4-diazabicyclo[2.2.2]octane, pyrazine, and mixtures thereof.

4. The method according to claim 3, characterized in that the coupling reaction of the compound [b] with the compound [d] is carried out in a solvent selected from the group consisting of dimethylsulfoxide and N,N-dimethylacetamide, in the presence of a copper catalyst selected from the group consisting of copper acetate, copper halide, copper nitrate and a copper salt of trifluoromethanesulfonic acid, in the presence or absence of one or more bases selected from the group consisting of triethylamine, diisopropylethylamine, tributylamine, tripropylamine, trioctylamine, dimethylbenzylamine, 1,8-diazabicyclo[5.4.0]undec-7-ene, N-ethylmorpholine, N-methylmorpholine, sodium hydrogen carbonate and an aqueous ammonia, in the presence or absence of one or more ligands selected from the group consisting of dimethylaminopyridine, 2-aminopyridine, 4-methylpyridine, 2,6-dimethylpyridine, 3,5-dimethylpyridine, pyridine, N-methylimidazole, N-butylimidazole and pyrazine, and under oxygen supply to the reaction system.

5. A compound of the following formula [b]:

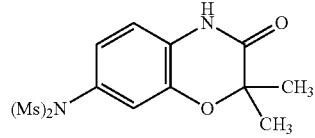
[b]

wherein Ms is a methanesulfonyl group.

6. A compound of the following formula [c]:

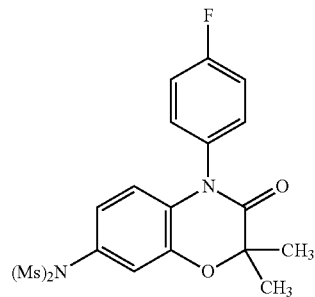
[c]

wherein Ms is a methanesulfonyl group.

* * * * *